US012044666B2

(12) United States Patent
Smith et al.

(10) Patent No.: US 12,044,666 B2
(45) Date of Patent: Jul. 23, 2024

(54) ULTRA-LIGHTWEIGHT, HANDHELD GAS LEAK DETECTION DEVICE

(71) Applicant: SEEKOPS INC., Austin, TX (US)

(72) Inventors: Brendan James Smith, Lakeway, TX (US); Garrett Niall John, Buda, TX (US); Andrew David Aubrey, Austin, TX (US); Anders Andelman Nottrott, Santa Barbara, CA (US); Victor Alexander Miller, II, Austin, TX (US)

(73) Assignee: SeekOps Inc., Austin, TX (US)

( * ) Notice: Subject to any disclaimer, the term of this patent is extended or adjusted under 35 U.S.C. 154(b) by 601 days.

(21) Appl. No.: 17/264,407

(22) PCT Filed: Jul. 30, 2019

(86) PCT No.: PCT/US2019/044119
§ 371 (c)(1),
(2) Date: Jan. 29, 2021

(87) PCT Pub. No.: WO2020/028353
PCT Pub. Date: Feb. 6, 2020

(65) Prior Publication Data
US 2022/0113290 A1    Apr. 14, 2022

Related U.S. Application Data

(60) Provisional application No. 62/712,096, filed on Jul. 30, 2018.

(51) Int. Cl.
*G01N 33/00* (2006.01)
*G01N 1/24* (2006.01)
*G01N 21/3504* (2014.01)

(52) U.S. Cl.
CPC .......... *G01N 33/0009* (2013.01); *G01N 1/24* (2013.01); *G01N 21/3504* (2013.01);
(Continued)

(58) Field of Classification Search
CPC .. G01N 1/24; G01N 33/0009; G01N 33/0011; G01N 33/0031; G01N 33/0016;
(Continued)

(56) References Cited

U.S. PATENT DOCUMENTS 3,780,566 A    12/1973   Smith et al.
4,135,092 A    1/1979    Milly
(Continued)

FOREIGN PATENT DOCUMENTS

AU    3401499    * 11/1999    ............ G01M 3/00
CN    104458588 A    3/2015
(Continued)

OTHER PUBLICATIONS

Manuel Queißer et al., Large-area quantification of subaerial CO2 anomalies with portable laser remote sensing and 2D tomography, The Leading Edge Mar. 2018, pp. 306-313 (Year: 2018).*
(Continued)

*Primary Examiner* — Stephanie E Bloss
*Assistant Examiner* — Kevin C Butler
(74) *Attorney, Agent, or Firm* — Concept IP LLP; Michael Zarrabian

(57) ABSTRACT

Systems, devices and methods including a handheld sensing device comprising: a sensor configured to measure ambient methane, ethane, propane, butane, and/or pentane concentrations; and a handle, where the sensor is disposed on a first end of the handle; control electronics comprising: a processor having addressable memory, the processor in communication with the sensor, where the processor is configured to: receive the measured ambient gas concentrations; and detect elevated ambient gas concentrations that may be attributed to a natural gas emissions source based on the measured ambient gas concentrations.

16 Claims, 13 Drawing Sheets

(52) U.S. Cl.
CPC ..... *G01N 33/0011* (2013.01); *G01N 33/0016* (2013.01); *G01N 33/0031* (2013.01); *G01N 2033/0068* (2013.01); *G01N 2201/0221* (2013.01)

(58) Field of Classification Search
CPC ....... G01N 21/3504; G01N 2033/0068; G01N 2201/0221
USPC .......................................................... 73/23.2
See application file for complete search history.

(56) References Cited

U.S. PATENT DOCUMENTS

| | | | |
|---|---|---|---|
| 4,233,564 A | 11/1980 | Kerbel | |
| 4,507,558 A * | 3/1985 | Bonne | G01N 21/031 250/343 |
| 4,988,833 A * | 1/1991 | Lai | H01B 7/065 174/69 |
| 5,047,639 A | 9/1991 | Wong | |
| 5,075,619 A | 12/1991 | Said | |
| 5,173,749 A | 12/1992 | Tell et al. | |
| 5,291,265 A | 3/1994 | Kebabian | |
| 5,317,156 A | 5/1994 | Cooper et al. | |
| 5,822,058 A | 10/1998 | Adler-Golden et al. | |
| 6,064,488 A | 5/2000 | Brand et al. | |
| 6,295,859 B1 | 10/2001 | Hayden et al. | |
| 6,509,566 B1 | 1/2003 | Wamsley et al. | |
| 6,549,630 B1 | 4/2003 | Bobisuthi | |
| 7,800,751 B1 | 9/2010 | Silver et al. | |
| 7,833,480 B2 | 11/2010 | Blazewicz et al. | |
| 8,060,270 B2 | 11/2011 | Vian et al. | |
| 8,294,899 B2 | 10/2012 | Wong | |
| 8,451,120 B2 * | 5/2013 | Johnson, Jr. | G08B 21/14 340/572.1 |
| 8,730,461 B2 | 5/2014 | Andreussi | |
| 9,183,371 B2 | 11/2015 | Narendra et al. | |
| 9,183,731 B1 * | 11/2015 | Bokhary | H04W 4/90 |
| 9,235,974 B2 | 1/2016 | Johnson, Jr. et al. | |
| 9,250,175 B1 | 2/2016 | McManus | |
| 9,494,511 B2 | 11/2016 | Wilkins | |
| 9,599,529 B1 | 3/2017 | Steele et al. | |
| 9,599,597 B1 | 3/2017 | Steele et al. | |
| 10,023,311 B2 | 7/2018 | Lai et al. | |
| 10,023,323 B1 | 7/2018 | Roberts et al. | |
| 10,031,040 B1 | 7/2018 | Smith et al. | |
| 10,126,200 B1 | 11/2018 | Steele et al. | |
| 10,268,198 B2 | 4/2019 | Mantripragada et al. | |
| 10,325,485 B1 | 6/2019 | Schuster | |
| 10,365,646 B1 | 7/2019 | Farnsworth et al. | |
| 10,429,546 B1 | 10/2019 | Ulmer | |
| 10,677,771 B2 | 6/2020 | Dittberner et al. | |
| 10,753,864 B2 | 8/2020 | Kasten et al. | |
| 10,816,458 B2 | 10/2020 | Kasten et al. | |
| 10,830,034 B2 | 11/2020 | Cooley et al. | |
| 10,962,437 B1 | 3/2021 | Nottrott et al. | |
| 11,105,784 B2 | 8/2021 | Kukreja et al. | |
| 11,112,308 B2 | 9/2021 | Kreitinger et al. | |
| 11,275,068 B2 | 3/2022 | Willett | |
| 11,299,268 B2 | 4/2022 | Christensen et al. | |
| 11,519,855 B2 | 12/2022 | Black et al. | |
| 11,557,212 B2 | 1/2023 | Hong | |
| 11,614,430 B2 | 3/2023 | Buckingham et al. | |
| 11,619,562 B2 | 4/2023 | Leen et al. | |
| 11,710,411 B2 | 7/2023 | Van Meeteren et al. | |
| 11,748,866 B2 | 9/2023 | Vargas | |
| 2002/0005955 A1 | 1/2002 | Kramer et al. | |
| 2003/0160174 A1 | 8/2003 | Grant et al. | |
| 2003/0189711 A1 | 10/2003 | Orr et al. | |
| 2003/0230716 A1 | 12/2003 | Russell et al. | |
| 2004/0012787 A1 | 1/2004 | Galle et al. | |
| 2004/0017762 A1 | 1/2004 | Sogawa et al. | |
| 2004/0212804 A1 | 10/2004 | Neff et al. | |
| 2006/0015290 A1 | 1/2006 | Warburton et al. | |
| 2006/0044562 A1 | 3/2006 | Hagene et al. | |
| 2006/0232772 A1 | 10/2006 | Silver | |
| 2006/0234621 A1 | 10/2006 | Desrochers et al. | |
| 2007/0137318 A1 | 6/2007 | Desrochers et al. | |
| 2008/0169934 A1 * | 7/2008 | Lang | G01N 33/0009 340/632 |
| 2008/0243372 A1 | 10/2008 | Bodin et al. | |
| 2009/0201507 A1 | 8/2009 | Kluczynski et al. | |
| 2009/0263286 A1 | 10/2009 | Isomura et al. | |
| 2009/0326792 A1 | 12/2009 | McGrath | |
| 2010/0004798 A1 | 1/2010 | Bodin et al. | |
| 2010/0131207 A1 | 5/2010 | Lippert et al. | |
| 2010/0140478 A1 | 6/2010 | Wilson et al. | |
| 2010/0147081 A1 | 6/2010 | Thomas | |
| 2011/0035149 A1 | 2/2011 | McAndrew et al. | |
| 2011/0074476 A1 | 3/2011 | Heer et al. | |
| 2011/0150035 A1 | 6/2011 | Hanson et al. | |
| 2011/0164251 A1 | 7/2011 | Richter | |
| 2011/0213554 A1 | 9/2011 | Archibald et al. | |
| 2011/0242659 A1 | 10/2011 | Eckles et al. | |
| 2011/0257944 A1 | 10/2011 | Du et al. | |
| 2012/0120397 A1 | 5/2012 | Furtaw et al. | |
| 2013/0044314 A1 | 2/2013 | Koulikov et al. | |
| 2013/0076900 A1 | 3/2013 | Mrozek et al. | |
| 2013/0208262 A1 | 8/2013 | Andreussi | |
| 2014/0172323 A1 | 6/2014 | Marino | |
| 2014/0204382 A1 | 7/2014 | Christensen | |
| 2014/0236390 A1 | 11/2014 | Mohamadi | |
| 2014/0336957 A1 | 11/2014 | Hanson et al. | |
| 2015/0072633 A1 | 3/2015 | Massarella et al. | |
| 2015/0145954 A1 | 5/2015 | Pulleti et al. | |
| 2015/0275114 A1 | 10/2015 | Tumiatti et al. | |
| 2015/0295543 A1 | 10/2015 | Brown et al. | |
| 2015/0316473 A1 | 11/2015 | Kester et al. | |
| 2015/0323449 A1 | 11/2015 | Jones et al. | |
| 2015/0336667 A1 | 11/2015 | Srivastava et al. | |
| 2016/0018373 A1 | 1/2016 | Page et al. | |
| 2016/0070265 A1 | 3/2016 | Liu et al. | |
| 2016/0104250 A1 | 4/2016 | Allen et al. | |
| 2016/0146696 A1 | 5/2016 | Steele et al. | |
| 2016/0161456 A1 | 6/2016 | Risk et al. | |
| 2016/0202225 A1 | 7/2016 | Feng et al. | |
| 2016/0214715 A1 | 7/2016 | Meffert | |
| 2016/0307447 A1 | 10/2016 | Johnson et al. | |
| 2016/0357192 A1 | 12/2016 | McGrew et al. | |
| 2017/0003684 A1 | 1/2017 | Knudsen et al. | |
| 2017/0057081 A1 | 3/2017 | Krohne et al. | |
| 2017/0089829 A1 | 3/2017 | Bartholomew et al. | |
| 2017/0093122 A1 | 3/2017 | Bean et al. | |
| 2017/0097274 A1 | 4/2017 | Thorpe et al. | |
| 2017/0115218 A1 | 4/2017 | Huang et al. | |
| 2017/0134497 A1 | 5/2017 | Harter et al. | |
| 2017/0158353 A1 | 6/2017 | Schmick | |
| 2017/0199647 A1 | 7/2017 | Richman et al. | |
| 2017/0206648 A1 | 7/2017 | Marra et al. | |
| 2017/0235018 A1 | 8/2017 | Foster et al. | |
| 2017/0259920 A1 | 9/2017 | Lai et al. | |
| 2017/0307519 A1 | 10/2017 | Black et al. | |
| 2017/0336281 A1 | 11/2017 | Waxman et al. | |
| 2017/0339820 A1 | 11/2017 | Foster et al. | |
| 2018/0023974 A1 | 1/2018 | Otani et al. | |
| 2018/0045561 A1 | 2/2018 | Leen et al. | |
| 2018/0045596 A1 | 2/2018 | Prasad et al. | |
| 2018/0050798 A1 | 2/2018 | Kapuria | |
| 2018/0059003 A1 | 3/2018 | Jourdainne et al. | |
| 2018/0067066 A1 | 3/2018 | Giedd et al. | |
| 2018/0109767 A1 | 4/2018 | Li et al. | |
| 2018/0122246 A1 | 5/2018 | Clark | |
| 2018/0127093 A1 | 5/2018 | Christensen et al. | |
| 2018/0188129 A1 | 7/2018 | Choudhury et al. | |
| 2018/0259955 A1 | 9/2018 | Noto | |
| 2018/0266241 A1 | 9/2018 | Ferguson et al. | |
| 2018/0266946 A1 | 9/2018 | Kotidis et al. | |
| 2018/0269902 A1 | 10/2018 | Myshak et al. | |
| 2018/0284088 A1 | 10/2018 | Verbeck, IV | |
| 2018/0292374 A1 | 10/2018 | Dittberner et al. | |
| 2018/0321692 A1 | 11/2018 | Castillo-Effen et al. | |
| 2018/0322699 A1 | 11/2018 | Gray et al. | |
| 2019/0011920 A1 | 1/2019 | Heinonen et al. | |
| 2019/0011935 A1 | 1/2019 | Ham et al. | |

(56) References Cited

U.S. PATENT DOCUMENTS

| | | | |
|---|---|---|---|
| 2019/0025199 A1 | 1/2019 | Koulikov | |
| 2019/0033194 A1 | 1/2019 | DeFreez et al. | |
| 2019/0049364 A1 | 2/2019 | Rubin | |
| 2019/0077506 A1 | 3/2019 | Shaw et al. | |
| 2019/0086202 A1 | 3/2019 | Guan et al. | |
| 2019/0095687 A1 | 3/2019 | Shaw et al. | |
| 2019/0154874 A1 | 5/2019 | Shams et al. | |
| 2019/0178743 A1 | 6/2019 | McNeil | |
| 2019/0195789 A1 | 6/2019 | Pan et al. | |
| 2019/0204189 A1 | 7/2019 | Mohr, Jr. et al. | |
| 2019/0212419 A1 | 7/2019 | Jeong et al. | |
| 2019/0220019 A1 | 7/2019 | Tan et al. | |
| 2019/0228573 A1 | 7/2019 | Sen et al. | |
| 2019/0234868 A1 | 8/2019 | Tanomura et al. | |
| 2019/0331652 A1 | 10/2019 | Ba et al. | |
| 2020/0050189 A1 | 2/2020 | Gu et al. | |
| 2020/0109976 A1 | 4/2020 | Ajay et al. | |
| 2020/0135036 A1 | 4/2020 | Campbell | |
| 2020/0249092 A1 | 8/2020 | Podmore et al. | |
| 2020/0400635 A1 | 12/2020 | Potyrailo et al. | |
| 2021/0017926 A1 | 1/2021 | Alkadi et al. | |
| 2021/0037197 A1 | 2/2021 | Kester et al. | |
| 2021/0055180 A1 | 2/2021 | Thorpe et al. | |
| 2021/0109074 A1* | 4/2021 | Smith | G01N 33/0062 |
| 2021/0140934 A1 | 5/2021 | Smith et al. | |
| 2021/0190745 A1* | 6/2021 | Buckingham | G01M 3/16 |
| 2021/0190918 A1 | 6/2021 | Li et al. | |
| 2021/0199565 A1 | 7/2021 | John et al. | |
| 2021/0247369 A1 | 8/2021 | Nottrott et al. | |
| 2021/0255158 A1 | 8/2021 | Smith et al. | |
| 2021/0300591 A1 | 9/2021 | Tian | |
| 2021/0321174 A1* | 10/2021 | Sun | G01N 21/01 |
| 2021/0364427 A1* | 11/2021 | Smith | G01N 21/031 |
| 2021/0382475 A1* | 12/2021 | Smith | B64C 39/024 |
| 2022/0082495 A1 | 3/2022 | Kreitinger et al. | |
| 2022/0113290 A1* | 4/2022 | Smith | G01M 3/205 |
| 2022/0268952 A1 | 8/2022 | Liang et al. | |
| 2022/0341806 A1* | 10/2022 | Miller, II | G01M 3/20 |
| 2022/0357231 A1 | 11/2022 | Nahata et al. | |
| 2023/0146441 A1 | 5/2023 | Donnat et al. | |
| 2023/0160789 A1 | 5/2023 | Donnat et al. | |
| 2023/0194487 A1* | 6/2023 | Buckingham | G01M 3/20 73/23.2 |
| 2023/0207070 A1 | 6/2023 | Donnat et al. | |
| 2023/0213413 A1 | 7/2023 | Mohr, Jr. et al. | |
| 2023/0274651 A1 | 8/2023 | McGuire et al. | |
| 2023/0392498 A1 | 12/2023 | Srivastav et al. | |

FOREIGN PATENT DOCUMENTS

| | | | | |
|---|---|---|---|---|
| CN | 205749271 U | * | 11/2016 | |
| CN | 205749271 U | | 11/2016 | |
| CN | 106769977 A | * | 5/2017 | |
| CN | 106769977 A | | 5/2017 | |
| CN | 107703075 A | * | 2/2018 | |
| CN | 109780452 A | | 5/2019 | |
| CN | 211508182 U | | 9/2020 | |
| CN | 112213443 A | | 1/2021 | |
| DE | 29601472 U1 | * | 5/1996 | G01N 33/0009 |
| DE | 69333010 | | 4/2004 | |
| DE | 102014013822 A1 | * | 3/2016 | G01M 3/04 |
| EP | 1371962 B1 | | 7/2011 | |
| FR | 3047073 B1 | | 8/2019 | |
| GB | 2538563 A | * | 11/2016 | G01N 21/3504 |
| JP | 200975823 A | | 4/2009 | |
| JP | 2009075823 A | * | 4/2009 | |
| JP | 2009075823 A | | 4/2009 | |
| KR | 101770254 B1 | * | 6/2017 | G01N 33/00 |
| KR | 20170062813 | * | 6/2017 | G01N 33/0047 |
| KR | 20170062813 A | | 6/2017 | |
| KR | 101770254 B1 | | 8/2017 | |
| TW | 522226 U | * | 5/2016 | |
| WO | 1999054700 A2 | | 10/1999 | |
| WO | WO-1999054700 | * | 10/1999 | G01M 3/002 |
| WO | WO-02066950 A1 | * | 8/2002 | G01M 1/225 |
| WO | 2008021311 A2 | | 2/2008 | |
| WO | WO-2008021311 A2 | * | 2/2008 | G01N 33/0009 |
| WO | 2015073687 A1 | | 5/2015 | |
| WO | 2016045791 A1 | | 3/2016 | |
| WO | 2016045791 A1 | | 3/2016 | |
| WO | WO-2016045791 | * | 3/2016 | G01M 3/04 |
| WO | 2016162673 A1 | | 10/2016 | |
| WO | 2017069979 A1 | | 4/2017 | |
| WO | 2018121478 A1 | | 7/2018 | |
| WO | 2018227153 A1 | | 12/2018 | |
| WO | 2019246280 A1 | | 12/2019 | |
| WO | 2020007684 A1 | | 1/2020 | |
| WO | WO-2020028353 A1 | * | 2/2020 | G01M 3/205 |
| WO | WO-2020086499 A1 | * | 4/2020 | B64C 39/024 |
| WO | 2020206020 A1 | | 10/2020 | |
| WO | WO-2020206006 A1 | * | 10/2020 | G01J 3/0264 |
| WO | WO-2021055902 A1 | * | 3/2021 | G01M 3/20 |
| WO | WO-2021158916 A1 | * | 8/2021 | G01N 21/031 |
| WO | WO-2022093864 A1 | * | 5/2022 | |
| WO | WO-2022211837 A1 | * | 10/2022 | G01N 21/39 |

OTHER PUBLICATIONS

Manuel Queißer et al., A new frontier in CO2 flux measurements using a highly portable DIAL laser system, Scientific Reports, DOI:10.1038/srep33834 1, Sep. 22, 2016, pp. 1-13 (Year: 2016).*
Siwen Liu et al., Development of a UAV-Based System to Monitor Air Quality over an Oil Field, Montana Technological University, Montana Tech Library Digital Commons @ Montana Tech Graduate Theses & Non-Theses, Fall 2018, pp. 1-85 (Year: 2018).*
Toru Miyama et al., Estimating allowable carbon emission for CO2 concentration stabilization using a GCM-based Earth system model, Geophysical Research Letters, vol. 36, L19709, doi:10.1029/2009GL039678, 2009, pp. 0094-8276 (Year: 2009).*
Nicholas C. Parazoo et al., Interpreting seasonal changes in the carbon balance of southern Amazonia using measurements of XCO2 and chlorophyll fluorescence from GOSAT, Geophysical Research Letters, vol. 40, 2829-2833, doi:10.1002/grl.50452, 2013, pp. 2829-2833 (Year: 2013).*
Christoph Kern et al., Spatial Distribution of Halogen Oxides in the Plume of Mount Pagan Volcano, Mariana Islands, Geophysical Research Letters 10.1029/2018GL079245, Sep. 27, 2018, pp. 9588-9596 (Year: 2018).*
J. Liao et al., Observations of inorganic bromine (HOBr, BrO, and Br2) speciation at Barrow, Alaska, in spring 2009, Journal of Geophysical Research, vol. 117, D00R16, doi:10.1029/2011JD016641, 2012, pp. 1-11 (Year: 2012).*
Mark A. Clilverd et al., Energetic particle injection, acceleration, and loss during the geomagnetic disturbances which upset Galaxy 15, Journal of Geophysical Research, vol. 117, A12213, doi:10.1029/2012JA018175, 2012, pp. 1-16 (Year: 2012).*
Clive Oppenheimer et al., Ultraviolet Sensing of Volcanic Sulfur Emissions, Elements (An International Magazine of Mineralogy, Geochemistry, and Petrology), Apr. 2010, vol. 6, pp. 87-92 (Year: 2010).*
International Search Report and Written Opinion for PCT/US2019/044119 mailed Oct. 17, 2019.
International Search Report and Written Opinion for PCT/US23/13893, mailed Jun. 30, 2023.
International Search Report and Written Opinion for PCT/US22/38951, mailed Nov. 28, 2022.
Kelly J F et al. "A capillary absorption spectrometer for stable carbon isotope ratio (C/C) analysis in very small samples", Review of Scientific Instruments, American Institute of Physics, 2 Huntington Quadrangle, Melville, NY 11747, vol. 83, No. 2, Feb. 1, 2012 (Feb. 1, 2012), pp. 23101-23101, XP012161835, ISSN: 0034-6748, DOI: 10.1063/1.3680593.
Krings et al., Atmos. Meas. Tech., 11, 721-739, Feb. 7, 2018.
Lilian Joly, The evolution of AMULSE (Atmospheric Measurements by Ultra-Light Spectrometer) and its interest in atmospheric applications. Results of the Atmospheric Profiles of GreenhousE gasEs (APOGEE) weather balloon release campaign for satellite

(56) References Cited

OTHER PUBLICATIONS retrieval validation, p. 1-28, Sep. 25, 2019, Atmospheric Measurement Techniques Discussion (Joly).
U.S. Appl. No. 62/687,147, filed Jun. 19, 2018, Brendan James Smith.
"Safesite Multi-Threat Detection System", Jul. 11, 2012 (Jul. 11, 2012), pp. 1-6, XP055245980.
International Search Report and Written Opinion for PCT/US19/38011 mailed Sep. 9, 2019.
International Search Report and Written Opinion for PCT/US19/38015, mailed Oct. 18, 2019.
International Search Report and Written Opinion for PCT/US19/44119, mailed Oct. 17, 2019.
International Search Report and Written Opinion for PCT/US20/26228 mailed Jul. 1, 2020.
International Search Report and Written Opinion for PCT/US20/26232 mailed Jun. 26, 2020.
International Search Report and Written Opinion for PCT/US20/26246 mailed Jun. 29, 2020.
International Search Report and Written Opinion for PCT/US20/51696, mailed Feb. 3, 2021.
International Search Report and Written Opinion for PCT/US2020/044978, mailed Oct. 26, 2020.
International Search Report and Written Opinion for PCT/US2021/016821 mailed Apr. 26, 2021.
International Search Report and Written Opinion for PCT/US2021/024177, mailed Jun. 23, 2021.
International Search Report and Written Opinion for PCT/US2021/056708, mailed Jan. 27, 2022.
International Search Report and Written Opinion for PCT/US21/42061, mailed Nov. 26, 2021.
International Search Report and Written Opinion for PCT/US21/44532, mailed Jan. 11, 2022.
International Search Report and Written Opinion for PCT/US21/56710, mailed Feb. 23, 2022.
International Search Report and Written Opinion of PCT/US19/57305, mailed Jan. 2, 2020.
International Search Report and Written Opinion of PCT/US20/54117, mailed Dec. 22, 2020.
Joly, "Atmospheric Measurements by Ultra-Light Spectrometer (AMULSE) Dedicated to Vertical Profile In Situ Measurements of Carbon Dioxide (CO2) Under Weather Balloons: Instrumental Development and Field Application," Sensors 2016, 16, 1609.
Khan, "Low Power Greenhouse Gas Sensors for Unmanned Aerial Vehicles", Remote Snse. 2012, 4, 1355-1368.
Villa. "An Overview of Small Unmanned Aerial Vehicles for Air Quality Measurements: Present Applications and Future Prospectives". Sensors. Web . Jul. 12, 2016.
White, "Development of an Unmanned Aerial Vehicle for the Measurement of Turbulence in the Atmospheric Boundary Layer", Atmosphere, v.8, issue 10, 195, pp. 1-25.
International Search Report and Written Opinion for PCT/US2023/023933 mailed Sep. 26, 2023.
IEEE Conference Paper, "Research of the high pressure jet performance of small size nozzle," ISBN : 978-1-5090-1087-5, Publication Date : Oct. 1, 2016, Conference dates Oct. 10, 2016 thru Oct. 12, 2016.[retrieved from the Internet] on Sep. 1, 2023 at 4:14pm.
International Search Report and Written Opinion for PCT/US23/23905 mailed Oct. 5, 2023.
Development of a mobile tracer correlation method for assessment of air emissions from landfills and other area sources, Atmospheric Environment 102 (2015) 323-330. T.A. Foster-Wittig et al. 2015.
Measurements of Methane Emissions from Landfills Using a Time Correlation Tracer Method Based on FTIR Absorption Spectroscopy, Environ. Sci. Technol. 2001, 35, 21-25, B. Galle et. al. 2001.
Feng, Lingbing, Nowak, Gen, O'Neill, T.J., Welsh, A.H."Cutoff; A spatio-temporal imputation method." Journal of Hydrology 519 (2014) : 3591-3605 (Year:2014).
Cabreira et al. "Survey on Coverage Path Planning with Unmanned Aerial Vehicles", published: Drones, published: Jan. 2019, pp. 1-38, year 2019.

* cited by examiner

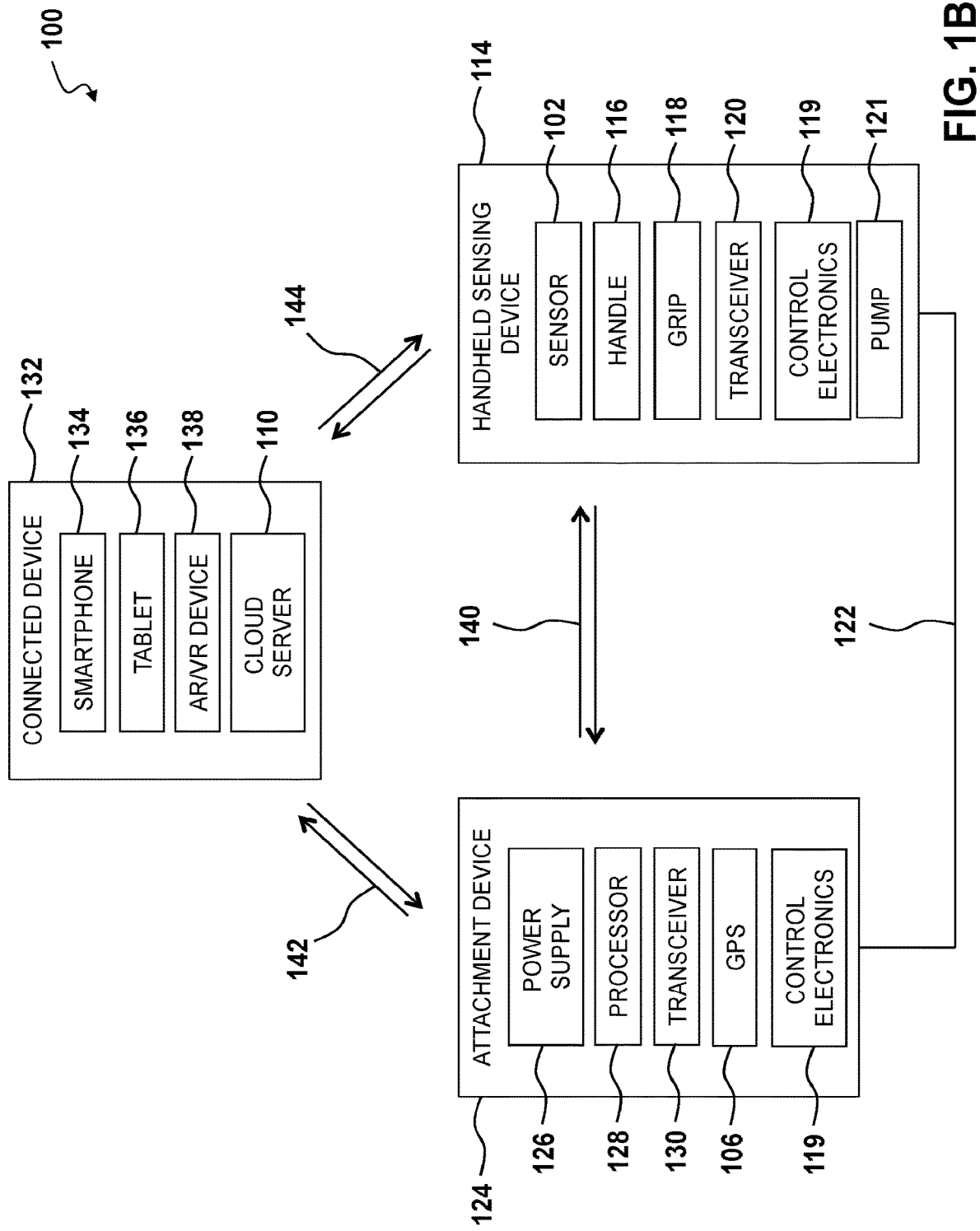

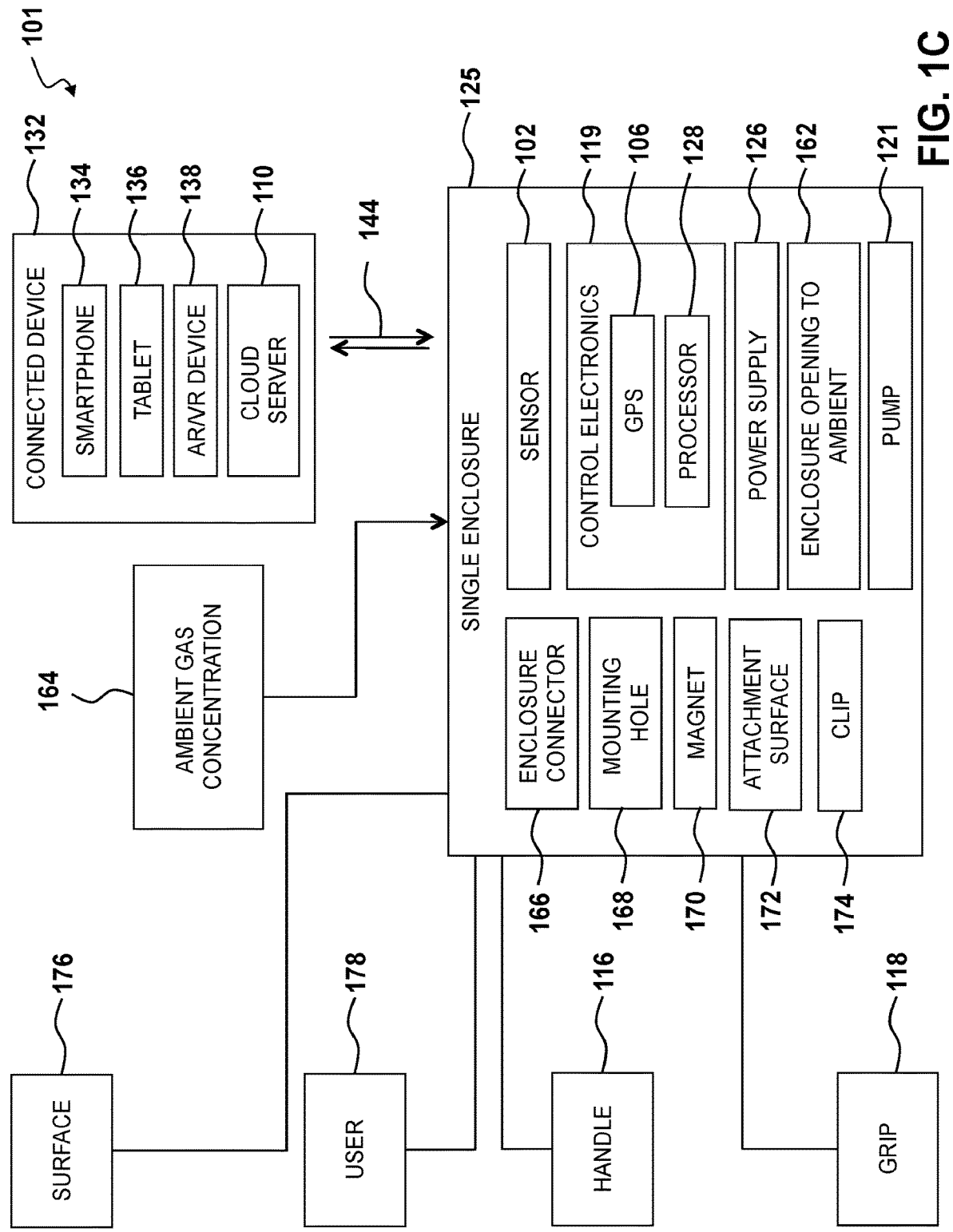

ULTRA-LIGHTWEIGHT, HANDHELD GAS LEAK DETECTION DEVICE

CROSS-REFERENCE TO RELATED APPLICATION

This application is a 35 U.S.C § 371 National State Entry of International Application No. PCT/US2019/044119, filed Jul. 30, 2019, which claims the priority benefit of U.S. Provisional Patent Application Ser. No. 62/712,096, filed Jul. 30, 2018, all of which are incorporated herein by reference in their entirety for all purposes.

FIELD OF ENDEAVOR

Embodiments relate generally to gas detection, and more particularly to methane gas detection.

BACKGROUND

Methane ($CH_4$) is an odorless and colorless naturally occurring organic molecule, which is present in the atmosphere at average ambient levels of approximately 1.85 ppm as of 2018 and is projected to continually climb. Methane is a powerful greenhouse gas, a source of energy (i.e., methane is flammable), and an explosion hazard, and so detection of methane is of utility to scientists as well as engineers. While methane is found globally in the atmosphere, a significant amount is collected or "produced" through anthropogenic processes including exploration, extraction, and distribution of petroleum resources as a component in natural gas. Natural gas, an odorless and colorless gas, is a primary fuel used to produce electricity and heat. The main component of natural gas is typically methane, and the concentration of methane in a stream of natural gas can range from about 70% to 90%. The balance of the gas mixture in natural gas consists of longer chain hydrocarbons, including ethane, propane, and butane, typically found in diminishing mole fractions that depend on the geology of the earth from which the gas is extracted. Once extracted from the ground, natural gas is processed into a product that must comply with specifications for both transport, taxation, and end-use in burners; specification of processed 'downstream' natural gas product control for the composition of the gas, so as to protect transport lines from corrosion and ensure proper operation of burners and turbines. While extraction of natural gas is one of the main sources of methane in the atmosphere, major contributors of methane also include livestock farming (i.e., enteric fermentation) and solid waste and wastewater treatment (i.e., anaerobic digestion). Anaerobic digestion and enteric fermentation gas products consist primarily of methane and lack additional hydrocarbon species.

SUMMARY

A system embodiment may include: a handheld sensing device comprising: a sensor configured to measure ambient gas concentrations of at least one of the following gasses: methane, ethane, propane, butane, and/or natural gas; and a handle, where the sensor may be disposed on a first end of the handle; an control electronics comprising: a processor having addressable memory, the processor in communication with the sensor, where the processor may be configured to: receive the measured ambient gas concentrations; and detect elevated ambient gas concentrations based on the measured ambient gas concentrations.

In additional system embodiments, the control electronics may be housed in an attachment device. In additional system embodiments, the control electronics may be housed inside the handle. In additional system embodiments, the sensor and control electronics may be housed in a single enclosure. In additional system embodiments, the sensor may measure a methane gas concentration. In additional system embodiments, the sensor measures at least one of the following gases: methane, ethane, propane, butane, and pentane. In additional system embodiments, the sensor measures at least two of the following gases: methane, ethane, propane, butane, and pentane. In additional system embodiments, the sensor measures a combination of gases that are representative of natural gas.

In additional system embodiments, the handheld sensing device further comprises: a grip disposed on a second end of the handle, where the first end of the handle may be distal from the second end of the handle. In additional system embodiments, the control electronics may be housed inside the grip. In additional system embodiments, the handheld sensing device further comprises: a first transceiver, where the processor may be in communication with the sensor via the first transceiver, and where the first transceiver may be configured to send measured ambient gas concentrations. In additional system embodiments, the attachment device further comprises: a second transceiver, where the processor may be in communication with the sensor via the first transceiver and the second transceiver, and where the second transceiver may be configured to receive measured ambient gas concentrations.

In additional system embodiments, the handheld sensing device may include: an single enclosure that contains both a sensor configured to measure gas concentration as well as the first transceiver. In this embodiment, the enclosure may be one of or a combination of the following devices to be used for fixing the sensor on a surface or body: holes to allow for a bolted joint connection to another surface; a magnet to fix the sensor to another surface; a surface on the enclosure itself which hook-and-loop/dual lock can be applied; a surface on the enclosure itself which an adhesive can be applied; a suction cup device; or a clip or other fastening device that can be used to clasp clothing worn by a person.

In additional system embodiments, the enclosure may be open to the ambient atmosphere, or it may be closed to the ambient atmosphere and a pump may be used to draw ambient gas sample into the chamber. In additional system embodiments, the system components may be located inside of the handle.

In additional system embodiments, the handheld sensing device may be connected to the attachment device via a wired connection. In additional system embodiments, the wired connection may be a shielded coiled cable. In additional system embodiments, the attachment device and/or control electronics may further comprise: a global positioning system (GPS). In additional system embodiments, the second transceiver may further comprise a GPS.

In additional system embodiments, the processor may be configured to: receive a location data from the GPS corresponding to the received measured ambient gas concentrations. In additional system embodiments, the processor may be configured to: receive a meteorological data corresponding to the received measured ambient gas concentrations. In additional system embodiments, the processor may be configured to: determine a location of a gas source based on the detected elevated ambient gas concentration, the received location data, and the received meteorological data.

Additional system embodiments may include: a connected device, where the connected device may be in communication with at least one of: the handheld sensing device, the attachment device, and the control electronics. In additional system embodiments, the connected device may acquire the location data from the GPS and relay it to at least one of: a first transceiver and a second transceiver. In additional system embodiments, the connected device may be configured to display a map showing the determined location of the gas source. In additional system embodiments, the connected device may include at least one of: a smartphone, a tablet, an augmented reality (AR) device, and a virtual reality (VR) device. In additional system embodiments, the connected device may be a cloud server having at least one database. In additional system embodiments, the attachment device further comprises: a power supply, where the power supply provides power to the handheld sensing device.

In additional system embodiments, a power supply may be located inside the grip, where the power supply may provide power to the handheld sensing device. In additional embodiments, a power supply may be located inside the handle, where the power supply may provide power to the handheld sensing device. In additional system embodiments, the sensor may be connected to a pump.

A method embodiment may include: measuring, by a sensor, ambient methane concentrations; receiving, by a processor having addressable memory, the measured ambient methane concentrations; and detecting, by the processor, elevated methane concentrations based on the measured ambient methane concentrations.

A method embodiment may include: measuring, by a sensor, ambient methane and ethane concentrations; receiving, by a processor having addressable memory, the measured ambient methane and ethane gas concentrations; and detecting, by the processor, elevated methane and ethane concentrations based on the measured ambient methane and ethane concentrations.

A method embodiment may include: measuring by a sensor, ambient gas concentrations; receiving, by a processor having addressable memory, the measured ambient gas concentrations; and detecting, by the processor, elevated gas concentrations based on the measured ambient gas concentrations A method embodiment may include: measuring by a sensor, ambient hydrocarbon gas concentrations, including any of the following gases: methane, ethane, propane, butane, or pentane; receiving, by a processor having addressable memory, the measured ambient hydrocarbon gas concentrations; and detecting, by the processor, elevated hydrocarbon gas concentrations based on the measured ambient hydrocarbon gas concentrations.

Additional method embodiments may include: receiving, by the processor, a location data from a global positioning system (GPS) corresponding to the received measured ambient gas concentrations; and receiving, by the processor, a meteorological data corresponding to the received measured ambient gas concentrations. Additional method embodiments may include: determining, by the processor, a location of a gas source based on the detected elevated ambient gas concentration, the received location data, and the received meteorological data. Additional method embodiments may include: displaying, by a connected device in communication with the processor, a map showing the determined location of the gas source.

Another system embodiment may include: a handheld sensing device comprising: a sensor configured to measure ambient gas concentrations; a handle, where the sensor may be disposed on a first end of the handle; a grip disposed on a second end of the handle, where the first end of the handle may be distal from the second end of the handle; and a first transceiver; an attachment device comprising: a second transceiver; a global positioning system (GPS); and a processor having addressable memory, the processor in communication with the sensor, where the processor may be configured to: receive the measured ambient gas concentrations; receive a location data from the GPS corresponding to the received measured ambient gas concentrations; receive a meteorological data corresponding to the received measured ambient gas concentrations; detect elevated ambient gas concentrations based on the measured ambient gas concentrations; determine a location of a gas source based on the detected elevated ambient gas concentration, the received location data, and the received meteorological data; where the processor may be in communication with the sensor via the first transceiver and the second transceiver, where the first transceiver may be configured to send measured ambient gas concentrations, and where the second transceiver may be configured to receive measured ambient gas concentrations a connected device, where the connected device may be in communication with at least one of: the handheld sensing device and the attachment device, where the connected device comprises at least one of: a smartphone, a tablet, an augmented reality (AR) device, and a virtual reality (VR) device, and where the connected device may be configured to display a map showing the determined location of the gas source.

BRIEF DESCRIPTION OF THE DRAWINGS

The components in the figures are not necessarily to scale, emphasis instead being placed upon illustrating the principals of the invention. Like reference numerals designate corresponding parts throughout the different views. Embodiments are illustrated by way of example and not limitation in the figures of the accompanying drawings, in which:

FIG. 1B shows a high-level block diagram of the handheld gas leak detection system, according to one embodiment;

FIG. 1C shows a high-level block diagram of another gas leak detection system, according to one embodiment;

DETAILED DESCRIPTION

The following description is made for the purpose of illustrating the general principles of the embodiments disclosed herein and is not meant to limit the concepts disclosed herein. Further, particular features described herein can be used in combination with other described features in each of the various possible combinations and permutations. Unless otherwise specifically defined herein, all terms are to be given their broadest possible interpretation including meanings implied from the description as well as meanings understood by those skilled in the art and/or as defined in dictionaries, treatises, etc.

The present system allows for a handheld sensor to collect methane concentration readings. The handheld sensor may include a sensor disposed on an end of a handle for detecting methane, or other gas, concentrations. The data from the sensor and location data may be combined to measure ambient gas concentrations of at least one of the following gasses: methane, ethane, propane, butane, and/or natural as a function of spatial coordinates, and to determine the location of an emission source of gas. This gas location may be displayed on a map and viewed on a connected device, such as a smartphone, tablet, augmented reality (AR), and/or virtual reality (VR) device. Because of the high fraction of methane in natural gas, a gas sensor capable of detecting methane can be used as a tool to identify and locate leaks of natural gas (using methane as a proxy), emanating from infrastructure associated with exploration, extraction, and distribution of natural gas. Furthermore, a trace gas sensor capable of measuring multiple hydrocarbon species typically found in natural gas can be used to determine whether a gas leak consists of natural gas (i.e., methane and ethane are detected simultaneously) or only methane, thereby attributing whether the source of the leak is natural gas infrastructure, or anaerobic digestion or enteric fermentation.

Figure 1A:
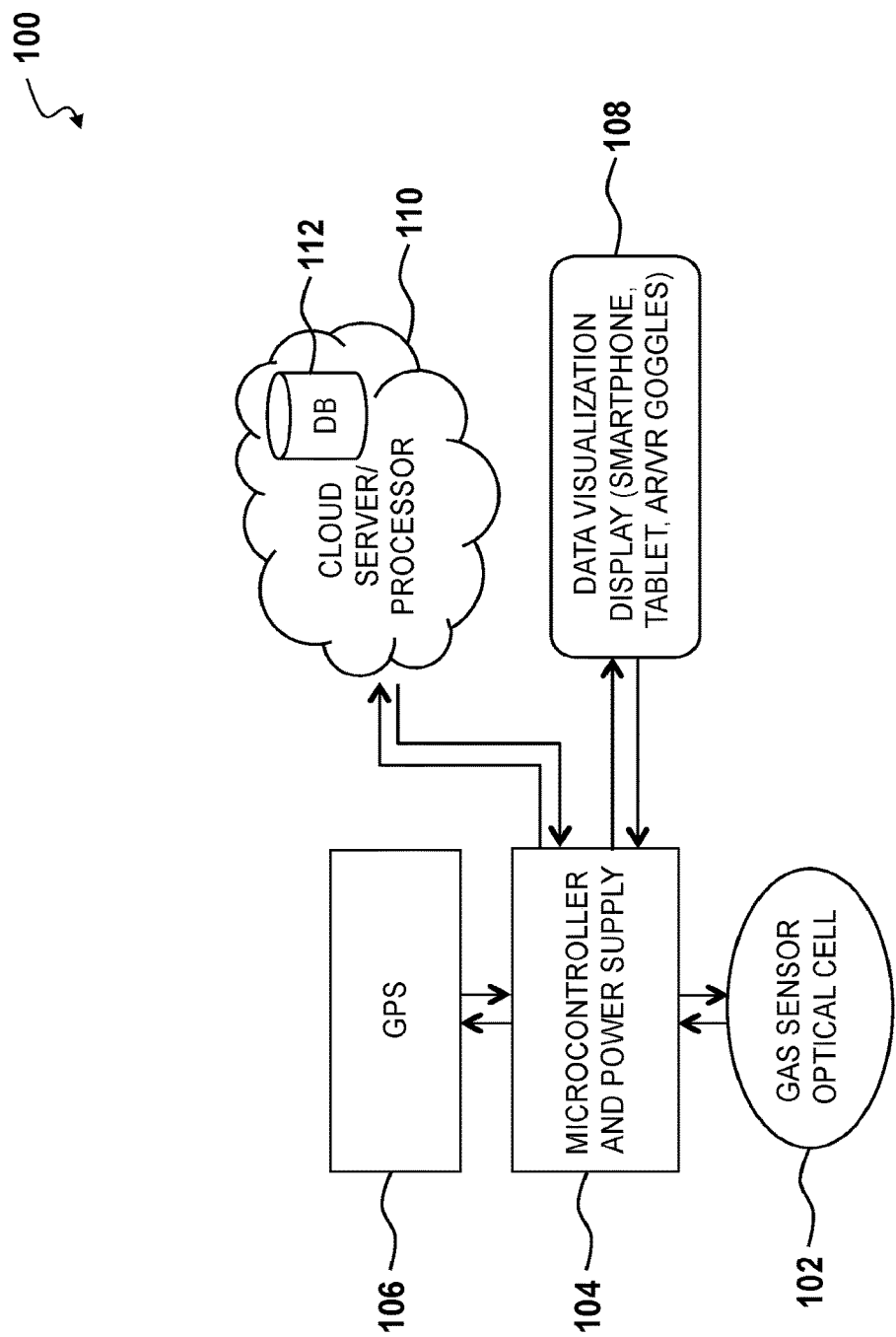
FIG. 1A shows a high-level block diagram and process of a handheld gas leak detection system, according to one embodiment.

FIG. 1A shows a high-level block diagram and process of a handheld gas leak detection system 100, according to one embodiment. The system 100 may include a sensor optical cell 102 for detecting ambient gas concentrations of at least one of the following gasses: methane, ethane, propane, butane, and/or natural gas. In one embodiment, the sensor optical cell 102 may detect methane ($CH_4$). Methane is an odorless and colorless naturally occurring organic molecule, which is present in the atmosphere at average ambient levels of approximately 1.85 ppm. While methane is found globally in the atmosphere, a significant amount is collected or "produced" through the exploration, drilling, and extraction of prehistoric sub-surface natural gas reserves. Natural gas, an odorless and colorless gas, is a primary source of energy used to produce electricity and heat. The concentration of methane in a stream of natural gas can range from about 70% to 90%. The balance of the gas mixture in natural gas consists of longer chain hydrocarbons, including ethane, propane, and butane, typically found in diminishing mole fractions that depend on the geology of the earth from which the gas is extracted. Once extracted from the ground, natural gas may be processed into a product that must comply with specifications for both transport, taxation, and end-use in burners. Specification of processed 'downstream' natural gas product control for the composition of gas, so as to protect transport lines from corrosion and ensure proper operation of burners and turbines. While extraction of natural gas is one of the main sources of methane in the atmosphere, major contributors of methane also include livestock farming, i.e., enteric fermentation, and solid waste and wastewater treatment, i.e., anaerobic digestion. Anaerobic digestion and enteric fermentation gas products consist primarily of methane and lack additional hydrocarbon species. Because of the high fraction of methane in natural gas, a gas sensor capable of detecting methane can be used as a tool to identify and locate leaks of natural gas (using methane as a proxy), emanating from infrastructure associate with exploration, extraction, and distribution of natural gas. Furthermore, a trace gas sensor capable of measuring multiple hydrocarbon species typically found in natural gas can be used to determine whether a gas leak consists of natural gas, i.e., methane and ethane are detected simultaneously, or only methane, thereby attributing whether the source of the leak is natural gas infrastructure, or anaerobic digestion or enteric fermentation.

The goal of the natural gas production and supply chain is to extract gas from source production areas and deliver it to endpoint users without undue loss. Product loss amounts to the venting of natural gas to the atmosphere. Undue product loss results in uncaptured revenue, increased environmental footprint, and possible safety hazards for vented emissions. There are many opportunities throughout the natural gas production and supply chain for gas to be released from containment and lost, e.g., pneumatic component venting, maintenance blowdowns, component failures, accidental release, etc. Because natural gas production and distribution infrastructure are spatially distributed, efficient survey methods are needed to identify, localize, and quantify natural gas releases throughout the system.

The sensor optical cell 102 may be an ultra-lightweight, low power, Part per Billion (ppb) sensitivity, mid-Infrared (wavelength $\lambda=3-8$ μm), open or closed path gas concentration sensor. The sampling rate of the cell 102 may be >0.1 Hz. The weight of the gas sensor optical cell 102 may be less than 500 g in some embodiments. In some embodiments, the optical cell 102 may be tuned for methane, ethane, propane, butane, pentane, carbon dioxide, carbon monoxide, hydrogen sulfide, ammonia, sulfur oxides, and/or nitrogen oxides.

The system 100 may also include a microcontroller and power supply 104. In some embodiments, the power supply may be a device, which may be integrated into a handle or mounted remotely from the sensor 102 and connected by cables to the sensor 102. The microcontroller may be a microcomputer that contains sensor firmware and low-level data processing functions, which may be mounted remotely from the sensor 102 and connected wirelessly or by cables to the sensor 102. In some embodiments, the power supply and/or microcontroller 104 may be connected to a utility belt, backpack, or other attachment, which may be worn by the user, or the power supply and/or microcontroller may be housed within the handle or enclosure. In some embodiments, the microcontroller 104 may be in communication with addressable memory to store data received from the sensor 102.

The system may include a GPS 106, which determines the location of the sensor 102 to combine the sensor readings with the geographic location for further processing. In some embodiments, a location sensor may be in place of, or in combination with, the GPS 106 to determine a geographic location of each sensor 102 reading. GPS information may also be collected from a connected device, such as a smartphone, tablet, wearable, and/or smartwatch; this GPS data may be fused with measurements made and processed by the sensor 102 and microcontroller 104. The data and/or readings from the sensor 102 and location from the GPS 106 may be processed by the microcontroller 104 and sent to a data visualization display 108 and/or a cloud server/processor 110 having at least one database 112. The data visualization display 108 may include a smartphone, a tablet, a portable computer, an augmented reality (AR) device, a smartwatch, and/or a virtual reality (VR) device. The AR/VR device may include goggles, a headset, wearables, or the like.

FIG. 1B shows a high-level block diagram of the handheld gas leak detection system 100, according to one embodiment. The system 100 includes a handheld sensing device 114 that may be carried by an operator for obtaining methane, or other gas concentration, measurements in different locations. The handheld sensing device 114 may include a sensor 102, a handle 116, and a grip 118. The handheld sensing device 114 is controlled by control electronics 119. In some embodiments, the control electronics may be contained in an attachment device 124, and the handheld sensing device 114 may communicate with an attachment device 124 via a wired connection 122 and/or a wireless connection 140. In some embodiments, the control electronics 119 may include a power supply 126, a processor 128 with addressable memory, a transceiver 130 or another communication device, and a GPS 106 or another location device in some embodiments. In other embodiments, the handheld sensing device 114 may communicate with the attachment device 124 via a wireless connection 140, such as via a transceiver 120, transmitter, radio, or the like. In some embodiments, the handheld sensing device 114 may communicate with the attachment device 124 via a wired connection 122 and/or a wireless connection 140. In some embodiments, the attachment device 124 may be integrated into the handheld sensing device 114 (See FIG. 7). In some embodiments, the handle 116 may be a shaft or stem element. In some embodiments, the sensor 102 may also be a closed-path measurement device, which requires gas to be sampled and pumped into the beam path within the optical core via a pump 121.

The sensor 102 may be disposed on an end of the handle 116 distal from a grip 118. The sensor 102 may be disposed proximate a first end of the handle 116. The grip 118 may be disposed proximate a second end of the handle 116, where the first end of the handle is distal from the second end of the handle 116. The handle 116 may have a length in the range of 3 to 90 inches in some embodiments. In some embodiments, the handle 116 may be curved. In some embodiments, the handle 116 may be extendible, and the extension may employ telescoping action. In some embodiments, at least a portion of the carry handle extension may be flexible to allow access in confined areas. In some embodiments, the handle 116 may include a weight or counterweight so as to provide a weight balance to the system 100, such as when being held by a user or operator of the system 100.

In some embodiments, the attachment device 124 may be attached to a belt, hip pack, backpack, or the like. The attachment device 124 may be worn by a user and connected to the handheld sensing device 114 via a wired connection 122 and/or wireless connection 140 for the unidirectional and/or bidirectional transfer of data. The attachment device 124 may include a power supply 126, a processor 128 with addressable memory, a transceiver 130 or another communication device, and a GPS 106 or another location device in some embodiments.

The processor 128 may perform processing on data from the sensor 102 and/or GPS 106. The disclosed handheld gas sensing device 114 is carried by a person, e.g., oil & gas equipment technician, field engineer, leak investigator, etc., during Leak Detection and Repair (LDAR) operations. The handheld sensing device 114 measures gas concentration within a gas sensor 102 to detect elevated ambient gas concentration associated with controlled or fugitive gas releases.

A connected device 132 may include a smartphone 134, tablet 136, portable computer, augmented reality (AR) or virtual reality (VR) device 138, and/or a cloud server 110. The data collected by the sensor 102 may be reconciled with measurements from a GPS 106 by the processor 128 and/or cloud server 110 to display information about methane concentration on a map via the connected device 132. The system 100 may display the source concentration data on a map, satellite image, aerial image, two-dimensional color map, two-dimensional contour map, and/or three-dimensional topographical surface/mesh. As the total methane concentration is inversely proportional to the distance from a source, this collected and processed data may be used to identify and locate gas sources within an inspection area. Search route guidance may direct the system operator toward the location of a gas leak, which may be automatically determined based on spatial concentration variability, atmospheric conditions, and weather data and/or meteorological data. The meteorological data may include current weather conditions and/or predicted future weather conditions. In some embodiments, search route guidance may be displayed visually to the system operator in real-time on a screen of the connected device 132 via the map or via AR/VR goggles 138.

The handheld sensing device 114, attachment device 124, and/or connected device 132 may communicate via wired 122 and/or wireless 140, 142, 144 connections.

Bidirectional data transfer 140, 142, 144 may occur between the handheld sensing device 114, the attachment device 124, and/or the connected device 132.

FIG. 1C shows a high-level block diagram of another gas leak detection system, according to one embodiment. In some embodiments, the sensor 102 and control electronics 119 may be contained in a single enclosure 125. In some embodiments, the single enclosure 125 may be open to the atmosphere, such as via an enclosure opening to ambient 162. In other embodiments, the single enclosure may be sealed from the atmosphere in all places except for a gas inlet. A pump 121 may be used in a sealed single enclosure 125 to draw an ambient gas sample 164 into a chamber of the sensor 102. The single enclosure 125 may contain a handle 116 in some embodiments. In other embodiments, the single enclosure 125 may be disposed in the handle 116. In some embodiments, the single enclosure 125 may be disposed in the grip 118. In some embodiments, the single enclosure 125 may include a power supply 126. In some embodiments, the control electronics 119 may include a GPS 106.

The single enclosure 119 may be fixed and/or detachably attached to a surface 176 and/or a person 178 by an enclosure connector 166. The enclosure connector 166 may include one or more mounting holes 168 that may be used to form a screwed or bolted joint connection. The enclosure connector 166 may also include a magnet 170, an attachment surface 172 for attaching hook and loop fasteners, dual lock, adhesive, or the like. In some embodiments, the single enclosure 119 may be detachably attached to a person 178 and/or surface 176, such as via a clip 174.

The single enclosure 125 may be in communication 144 with the connected device 132. The connected device 132 may include a smartphone 134, tablet 136, portable computer, augmented reality (AR) or virtual reality (VR) device 138, and/or a cloud server 110. The data collected by the sensor 102 may be reconciled with measurements from a GPS 106 to display information about gas concentration and/or gas source location on a map via the connected device 132. The system 100 may display the source concentration data on a map, satellite image, aerial image, two-dimensional color map, two-dimensional contour map, and/or three-dimensional topographical surface/mesh. As the total gas concentration is inversely proportional to the distance from a source, this collected and processed data may be used to identify and locate gas sources within an inspection area. Search route guidance may direct the system operator toward the location of a gas leak, which may be automatically determined based on spatial concentration variability, atmospheric conditions and weather data and/or meteorological data. The meteorological data may include current weather conditions and/or predicted future weather conditions. In some embodiments search route guidance may be displayed visually to the system operator in real-time on a screen of the connected device 132 via the map or via AR/VR goggles 138. In some embodiments, the connected device 132 may provide spatial and/or GPS location, such as via a GPS of the smartphone 134 that can be combined with the gas data from the sensor 102.

Figure 1D:
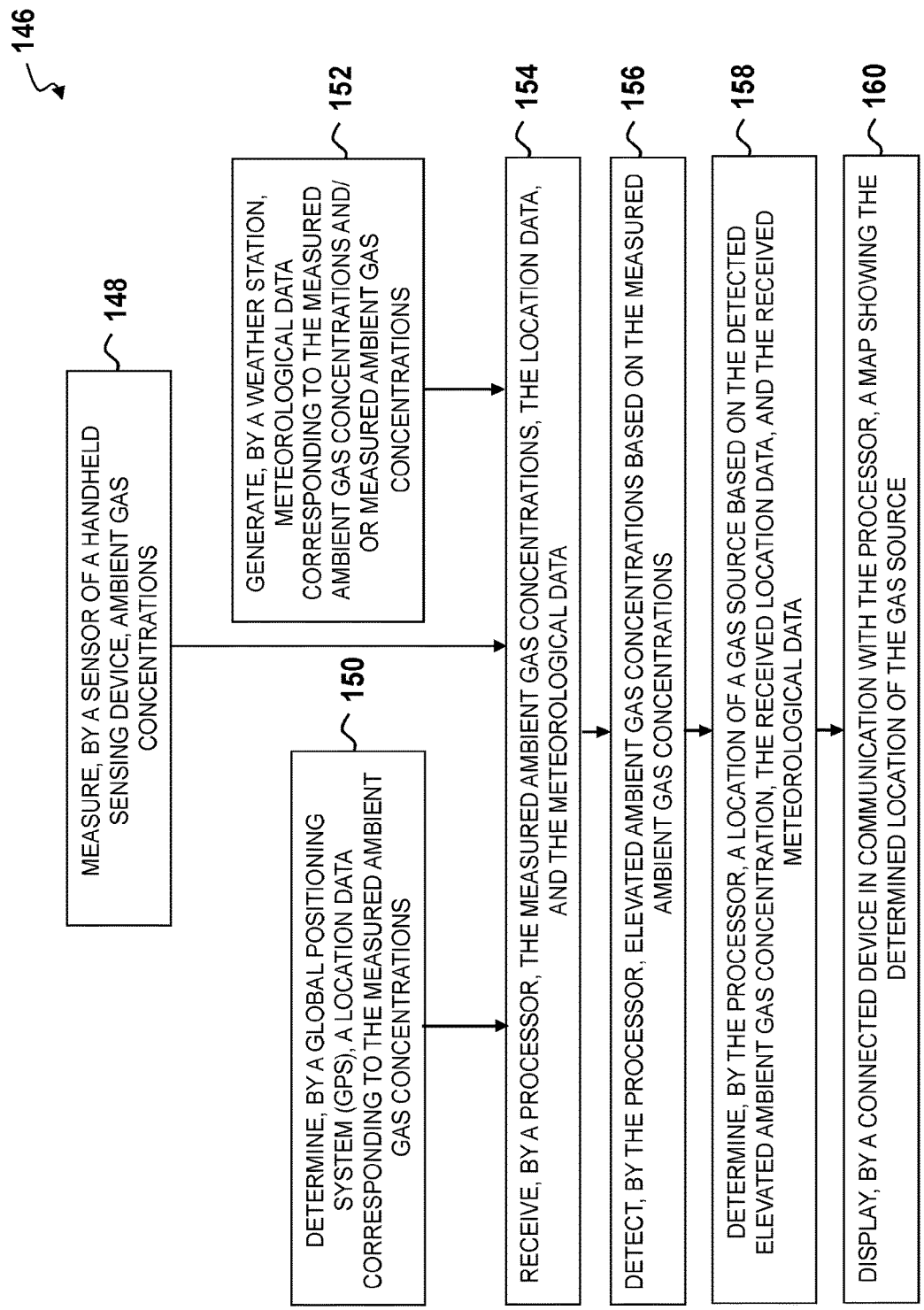
FIG. 1D depicts a high-level flowchart of a method embodiment of elevated ambient gas concentrations based on the measured ambient gas concentrations via a handheld gas leak detection system, according to one embodiment.

FIG. 1D depicts a high-level flowchart of a method embodiment 146 of elevated gas concentrations based on the measured ambient gas concentrations via a handheld gas leak detection system, according to one embodiment. The method 146 may include measuring, by a sensor of a handheld sensing device, ambient gas concentrations (step 148). The ambient gas concentrations may include at least one of the following gasses: methane, ethane, propane, butane, and/or natural gas. The handheld sensing device may be as shown in FIGS. 1A-1C. The method 146 may also include determining, by a global positioning system (GPS), a location data corresponding to the measured ambient gas concentrations (step 150). In some embodiments, a location sensor may be used in place of, or in combination with, the GPS to determine the location of the handheld sensing device such that each ambient gas concentration may be associated with a corresponding location data. The method 146 may then include generating, by a weather station, meteorological data corresponding to the measured ambient gas concentrations and/or measured ambient gas concentrations (step 152). The meteorological data may include current data, past data, and/or predicted future data.

Figure 7:
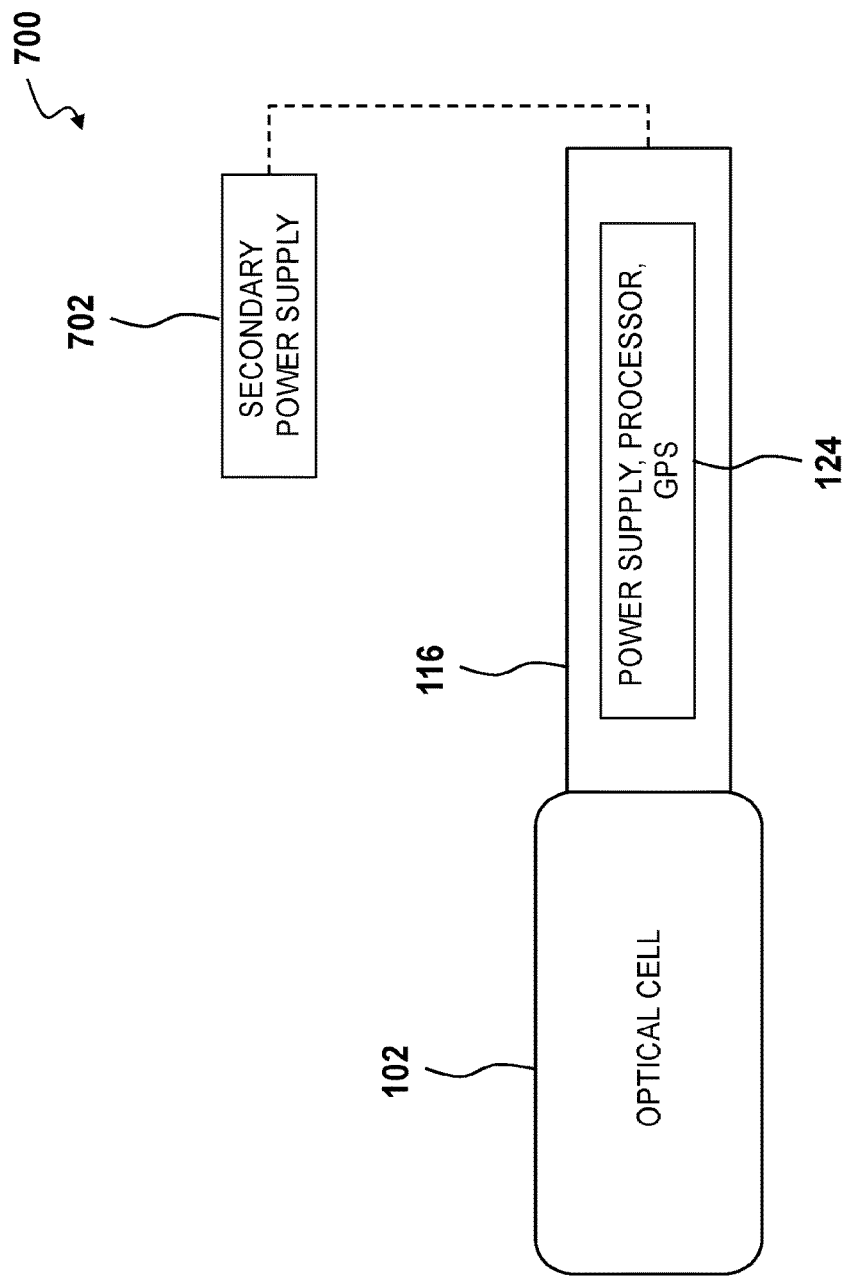
FIG. 7 depicts a block diagram of a handheld concentration measurement instrument with a built-in power supply and processing unit.

The method 146 may then include receiving, by a processor, the measured ambient gas concentrations, the location data, and the meteorological data (step 154). The processor may have addressable memory and be located in an attachment device, as shown in FIG. 1B. In other embodiments, the processor may be integrated into the handheld sensing device, as shown in FIG. 7. The method 146 may then include detecting, by the processor, elevated ambient gas concentrations based on the measured ambient gas concentrations (step 156). An optical cell in the handheld sensing device, as shown in FIG. 3, may record readings of gas concentrations elevated above an ambient level.

The method 146 may then include determining, by the processor, a location of a gas source based on the detected elevated ambient gas concentration, the received location data, and the received meteorological data (step 158). The processor may aggregate the location data, elevated gas readings, and meteorological data to determine a likely source location of the gas, such as a location of a gas leak in a gas equipment. The location of the gas may be a natural gas source. The method 146 may then include displaying, by a connected device in communication with the processor, a map showing the determined location of the gas source (step 160). The connected device may be a smartphone, laptop, tablet, augmented reality (AR) device, virtual reality (VR) device, and/or a cloud server having a database. In some embodiments, an operator may use AR or VR to view the location of the gas source. For example, by using AR goggles, the operator may identify the gas source as originating from a leak in gas equipment, such as natural gas equipment. The operator may then use the location of the gas leak to take corrective action such as to minimize or eliminate the source of the leak.

Figure 2:
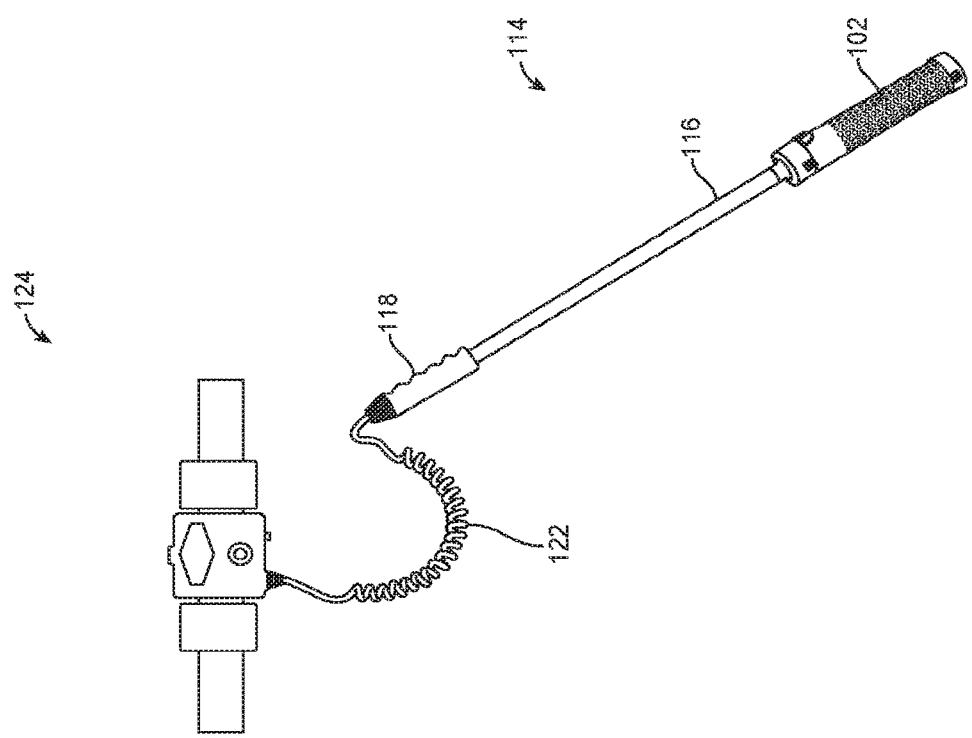
FIG. 2 depicts a handheld gas sensor and accompanying belt pack of the disclosed handheld gas leak detection system, according to one embodiment.

FIG. 2 depicts a handheld gas sensing device 114 and accompanying belt pack of the attachment device 124 of the disclosed handheld gas leak detection system, according to one embodiment. The handheld sensing device 114 may be tethered 122 with a wired connection 122, such as a shielded coiled cable to an accompanying attachment device 124, such as a belt pack worn by the system operator. The belt pack may house the power supply for the sensor 102 as well as an onboard microcomputer, which may run the system firmware and software. The data from the attachment device 124 may then be passed via a secure connection to a cloud server/processor and/or mobile connected device (See FIGS. 1B-1C). The cloud server may run advanced analytics and data processing software, while the mobile device may display the user interface, maps, and/or data visualization to the operator.

Figure 3:
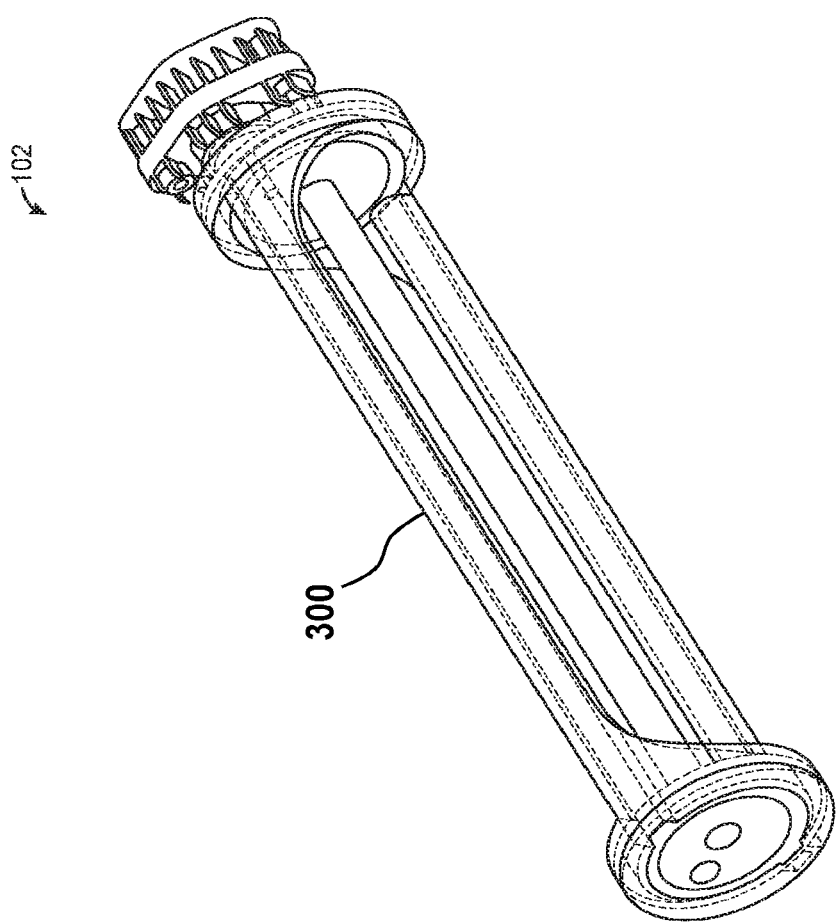
FIG. 3 depicts a handheld methane sensor optical core of the disclosed handheld gas leak detection system, according to one embodiment.

FIG. 3 depicts a handheld gas sensor 102 optical core 300 of the disclosed handheld gas leak detection system, according to one embodiment. The core 300 may be a self-contained Herriott cell design, utilizing tunable laser spectroscopy to detect gaseous molecules with high sensitivity. The optical core 300 may be an open-path measurement device and requires the passage of gaseous molecules through the optical cavity for detection to be made. The optical core 300 may also be a closed-path measurement device, which requires gas to be sampled and pumped into the beam path within the optical core 300. The optical core 300 may maintain sensor alignment, dampen vibrations, and conceal all sensor wiring through supporting conduits running along the outside of the cell. The optical core 300 may be designed to be both lightweight and compact for ease of use and versatility of application.

Figure 4:
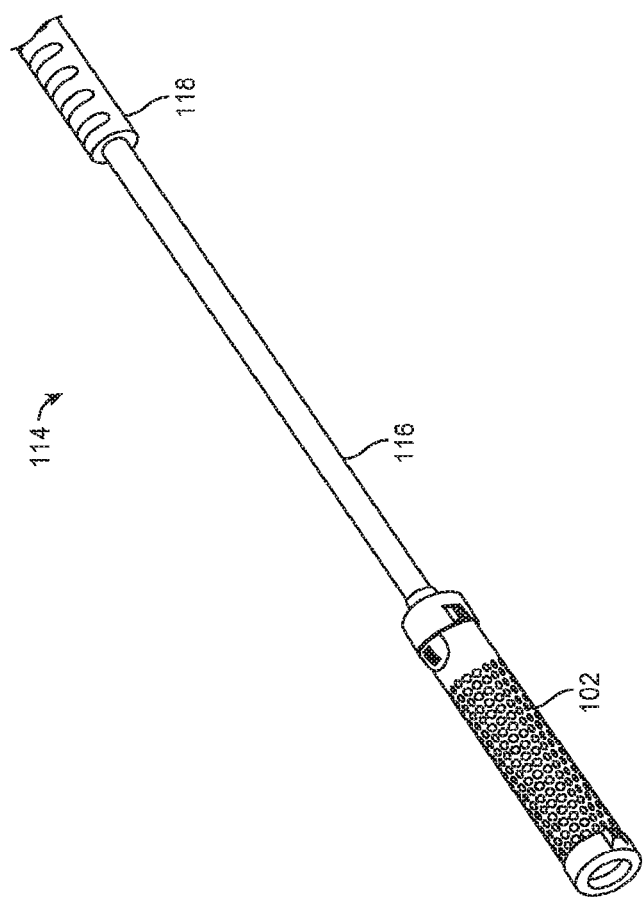
FIG. 4 depicts an ergonomic carry handle grip with an extension of the disclosed handheld gas leak detection system, according to one embodiment.

FIG. 4 depicts an ergonomic carry handle grip handheld sensing device 114 with an extension of the disclosed handheld gas leak detection system, according to one embodiment. The sensor optical core (See FIG. 3) may be mounted to an ergonomic carry handle grip with an extension to facilitate the measurement process. The handle 116 enables the surveyor to access an area of interest with minimal effort. The extension provides the user an optimal reach for both ground level and overhead sources. The carry handle of the handheld sensing device 114 is equipped with an ergonomic handgrip 118 designed with user comfort in mind.

Figure 5:
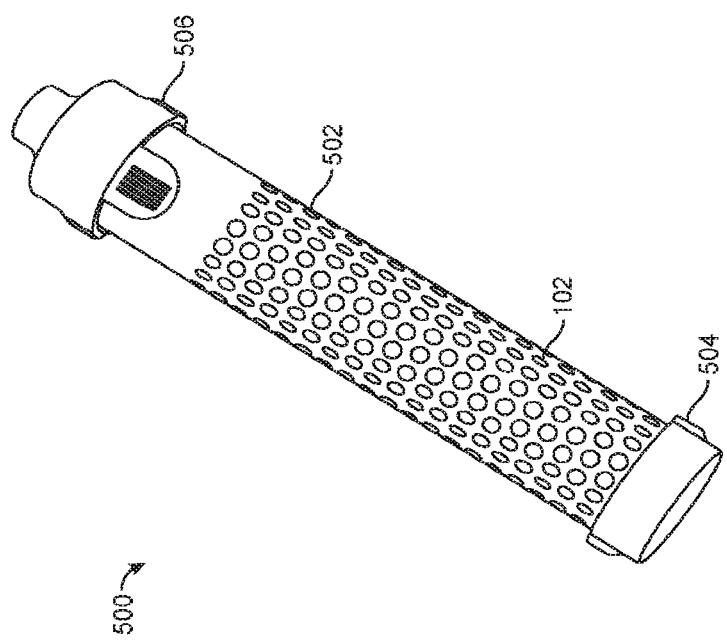
FIG. 5 depicts a protective housing of the optical core of the disclosed handheld gas leak detection system, according to one embodiment.

FIG. 5 depicts a protective housing 500 of the optical core of the disclosed handheld gas leak detection system, according to one embodiment. The optical core (See FIG. 3) is contained within the protective housing 500 to prevent any damage to the sensor 102 and electronics. The protective housing 500 may include a perforated outer sheath 502 and end caps 504, 506. The perforated sheath 502 may include a plurality of apertures that protects the optical cell from damaging impacts, deflects debris and allows for ample airflow to pass through the sensor core. In some embodiments, the sheath may be a perforated cover or wrapping element. In some embodiments, the perforated sheath 502 may include a cloth mesh and/or a fine metal mesh, which may be used to reduce water ingress to allow gas flow The end caps 504, 506 contain the optical cell and sensor 102 within the protective cover 502. In some embodiments, the perforated sheath 502 may be detachably attached to the end caps 504, 506 such that the perforated sheath 502, end caps 504, 506, and/or optical core may be replaced.

Figure 6:
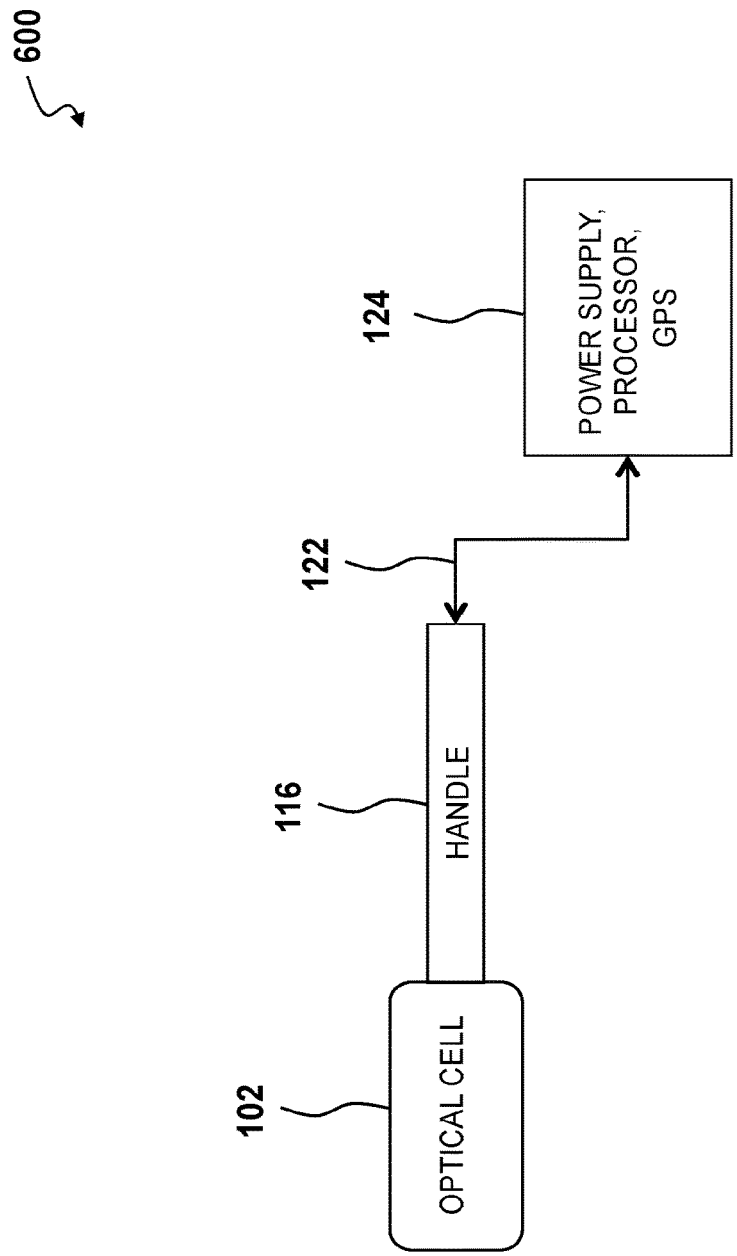
FIG. 6 depicts a block diagram of a handheld concentration measurement instrument with a remote power supply and processing unit, according to one embodiment.

FIG. 6 depicts a block diagram of a handheld concentration measurement instrument 600 with a remote power supply, processing unit, and/or GPS as an attachment device 124, according to one embodiment. The attachment device 124 may be contained in a device detachably attached to a belt, a hip pack, a backpack, or the like to reduce the weight of the handheld sensor with optical cell 102 and handle 116 and to allow ease of use by an operator.

FIG. 7 depicts a block diagram of a handheld concentration measurement instrument 700 with a built-in power supply and processing unit 124. The attachment device 124 may be integrated into a handle 116 of the handheld sensor to allow for a more compact form-factor. In some embodiments, the handheld sensor may include an additional attachment to a secondary power supply 702 to increase the working time of the handheld sensor without increasing the weight of the handheld sensor significantly.

Figure 8:
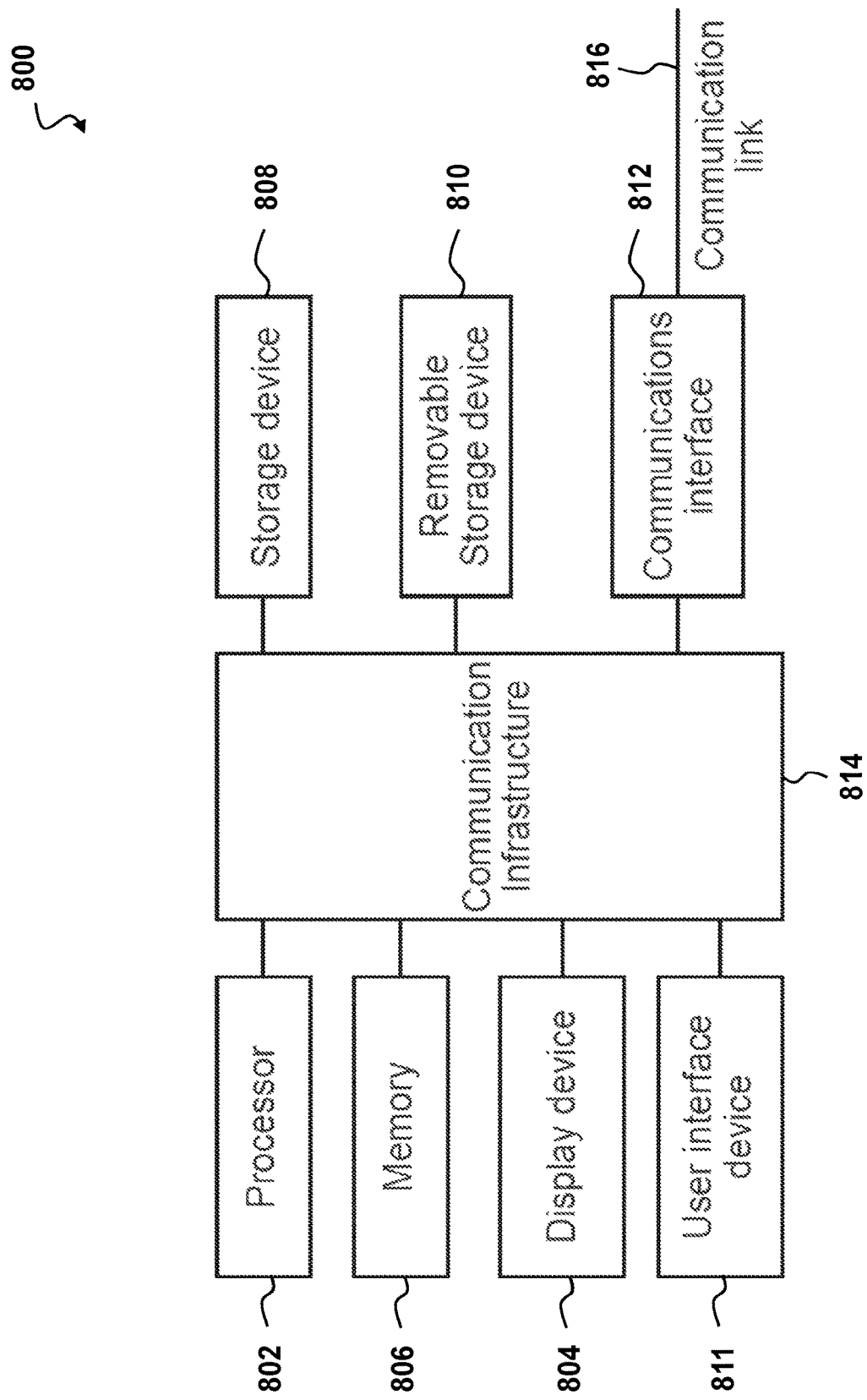
FIG. 8 shows a high-level block diagram and process of a computing system for implementing an embodiment of the system and process.

FIG. 8 is a high-level block diagram 800 showing a computing system comprising a computer system useful for implementing an embodiment of the system and process, disclosed herein. Embodiments of the system may be implemented in different computing environments. The computer system includes one or more processors 802, and can further include an electronic display device 804 (e.g., for displaying graphics, text, and other data), a main memory 806 (e.g., random access memory (RAM)), storage device 808, a removable storage device 810 (e.g., removable storage drive, a removable memory module, a magnetic tape drive, an optical disk drive, a computer readable medium having stored therein computer software and/or data), user interface device 811 (e.g., keyboard, touch screen, keypad, pointing device), and a communication interface 812 (e.g., modem, a network interface (such as an Ethernet card), a communications port, or a PCMCIA slot and card). The communication interface 812 allows software and data to be transferred between the computer system and external devices. The system further includes a communications infrastructure 814 (e.g., a communications bus, cross-over bar, or network) to which the aforementioned devices and modules are connected as shown.

Information transferred via communications interface 814 may be in the form of signals such as electronic, electromagnetic, optical, or other signals capable of being received by communications interface 814, via a communication link 816 that carries signals and may be implemented using wire or cable, fiber optics, a phone line, a cellular/mobile phone link, a radio frequency (RF) link, and/or other communication channels. Computer program instructions representing the block diagram and/or flowcharts herein may be loaded onto a computer, programmable data processing apparatus, or processing devices to cause a series of operations performed thereon to produce a computer implemented process.

Embodiments have been described with reference to flowchart illustrations and/or block diagrams of methods, apparatus (systems) and computer program products according to embodiments. Each block of such illustrations/diagrams, or combinations thereof, can be implemented by computer program instructions. The computer program instructions when provided to a processor produce a machine, such that the instructions, which execute via the processor, create means for implementing the functions/operations specified in the flowchart and/or block diagram. Each block in the flowchart/block diagrams may represent a hardware and/or software module or logic, implementing embodiments. In alternative implementations, the functions noted in the blocks may occur out of the order noted in the figures, concurrently, etc.

Computer programs (i.e., computer control logic) are stored in main memory and/or secondary memory. Computer programs may also be received via a communications interface 812. Such computer programs, when executed, enable the computer system to perform the features of the embodiments as discussed herein. In particular, the computer programs, when executed, enable the processor and/or multi-core processor to perform the features of the computer system. Such computer programs represent controllers of the computer system.

Figure 9:
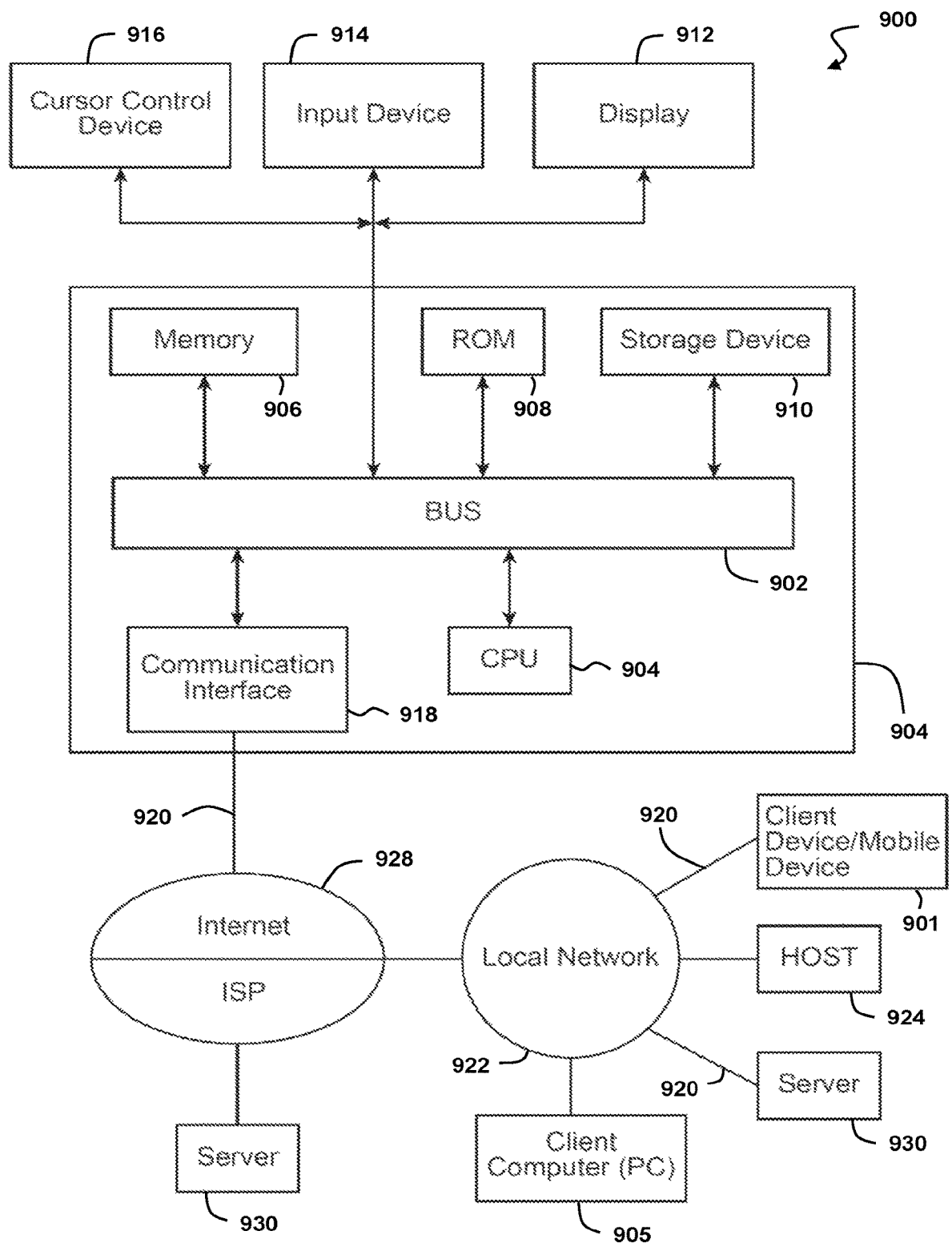
FIG. 9 shows a block diagram and process of an exemplary system in which an embodiment may be implemented.

FIG. 9 shows a block diagram of an example system 900 in which an embodiment may be implemented. The system 900 includes one or more client devices 901 such as consumer electronics devices, connected to one or more server computing systems 930. A server 930 includes a bus 902 or other communication mechanism for communicating information, and a processor (CPU) 904 coupled with the bus 902 for processing information. The server 930 also includes a main memory 906, such as a random access memory (RAM) or other dynamic storage device, coupled to the bus 902 for storing information and instructions to be executed by the processor 904. The main memory 906 also may be used for storing temporary variables or other intermediate information during execution or instructions to be executed by the processor 904. The server computer system 930 further includes a read only memory (ROM) 908 or other static storage device coupled to the bus 902 for storing static information and instructions for the processor 904. A storage device 910, such as a magnetic disk or optical disk, is provided and coupled to the bus 902 for storing information and instructions. The bus 902 may contain, for example, thirty-two address lines for addressing video memory or main memory 906. The bus 902 can also include, for example, a 32-bit data bus for transferring data between and among the components, such as the CPU 904, the main memory 906, video memory and the storage 910. Alternatively, multiplex data/address lines may be used instead of separate data and address lines.

The server 930 may be coupled via the bus 902 to a display 912 for displaying information to a computer user. An input device 914, including alphanumeric and other keys, is coupled to the bus 902 for communicating information and command selections to the processor 904. Another type or user input device comprises cursor control 916, such as a mouse, a trackball, or cursor direction keys for communicating direction information and command selections to the processor 904 and for controlling cursor movement on the display 912.

According to one embodiment, the functions are performed by the processor 904 executing one or more sequences of one or more instructions contained in the main memory 906. Such instructions may be read into the main memory 906 from another computer-readable medium, such as the storage device 910. Execution of the sequences of instructions contained in the main memory 906 causes the processor 904 to perform the process steps described herein. One or more processors in a multi-processing arrangement may also be employed to execute the sequences of instructions contained in the main memory 906. In alternative embodiments, hard-wired circuitry may be used in place of or in combination with software instructions to implement the embodiments. Thus, embodiments are not limited to any specific combination of hardware circuitry and software.

The terms "computer program medium," "computer usable medium," "computer readable medium", and "computer program product," are used to generally refer to media such as main memory, secondary memory, removable storage drive, a hard disk installed in hard disk drive, and signals. These computer program products are means for providing software to the computer system. The computer readable medium allows the computer system to read data, instructions, messages or message packets, and other computer readable information from the computer readable medium. The computer readable medium, for example, may include non-volatile memory, such as a floppy disk, ROM, flash memory, disk drive memory, a CD-ROM, and other permanent storage. It is useful, for example, for transporting information, such as data and computer instructions, between computer systems. Furthermore, the computer readable medium may comprise computer readable information in a transitory state medium such as a network link and/or a network interface, including a wired network or a wireless network that allow a computer to read such computer readable information. Computer programs (also called computer control logic) are stored in main memory and/or secondary memory. Computer programs may also be received via a communications interface. Such computer programs, when executed, enable the computer system to perform the features of the embodiments as discussed herein. In particular, the computer programs, when executed, enable the processor multi-core processor to perform the features of the computer system. Accordingly, such computer programs represent controllers of the computer system.

Generally, the term "computer-readable medium" as used herein refers to any medium that participated in providing instructions to the processor 904 for execution. Such a medium may take many forms, including but not limited to, non-volatile media, volatile media, and transmission media. Non-volatile media includes, for example, optical or magnetic disks, such as the storage device 910. Volatile media includes dynamic memory, such as the main memory 906. Transmission media includes coaxial cables, copper wire and fiber optics, including the wires that comprise the bus 902. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, an EPROM, a FLASH-EPROM, any other memory chip or cartridge, a carrier wave as described hereinafter, or any other medium from which a computer can read.

Various forms of computer readable media may be involved in carrying one or more sequences of one or more instructions to the processor 904 for execution. For example, the instructions may initially be carried on a magnetic disk of a remote computer. The remote computer can load the instructions into its dynamic memory and send the instructions over a telephone line using a modem. A modem local to the server 930 can receive the data on the telephone line and use an infrared transmitter to convert the data to an infrared signal. An infrared detector coupled to the bus 902 can receive the data carried in the infrared signal and place the data on the bus 902. The bus 902 carries the data to the main memory 906, from which the processor 904 retrieves and executes the instructions. The instructions received from the main memory 906 may optionally be stored on the storage device 910 either before or after execution by the processor 904.

The server 930 also includes a communication interface 918 coupled to the bus 902. The communication interface 918 provides a two-way data communication coupling to a network link 920 that is connected to the world wide packet data communication network now commonly referred to as the Internet 928. The Internet 928 uses electrical, electromagnetic or optical signals that carry digital data streams. The signals through the various networks and the signals on the network link 920 and through the communication interface 918, which carry the digital data to and from the server 930, are exemplary forms or carrier waves transporting the information.

In another embodiment of the server 930, interface 918 is connected to a network 922 via a communication link 920. For example, the communication interface 918 may be an integrated services digital network (ISDN) card or a modem to provide a data communication connection to a corresponding type of telephone line, which can comprise part of the network link 920. As another example, the communication interface 918 may be a local area network (LAN) card to provide a data communication connection to a compatible LAN. Wireless links may also be implemented. In any such implementation, the communication interface 918 sends and receives electrical electromagnetic or optical signals that carry digital data streams representing various types of information.

The network link 920 typically provides data communication through one or more networks to other data devices. For example, the network link 920 may provide a connection through the local network 922 to a host computer 924 or to data equipment operated by an Internet Service Provider (ISP). The ISP in turn provides data communication services through the Internet 928. The local network 922 and the Internet 928 both use electrical, electromagnetic or optical signals that carry digital data streams. The signals through the various networks and the signals on the network link 920 and through the communication interface 918, which carry the digital data to and from the server 930, are exemplary forms or carrier waves transporting the information.

The server 930 can send/receive messages and data, including e-mail, program code, through the network, the network link 920 and the communication interface 918. Further, the communication interface 918 can comprise a USB/Tuner and the network link 920 may be an antenna or cable for connecting the server 930 to a cable provider, satellite provider or other terrestrial transmission system for receiving messages, data and program code from another source.

The example versions of the embodiments described herein may be implemented as logical operations in a distributed processing system such as the system 900 including the servers 930. The logical operations of the embodiments may be implemented as a sequence of steps executing in the server 930, and as interconnected machine modules within the system 900. The implementation is a matter of choice and can depend on performance of the system 900 implementing the embodiments. As such, the logical operations constituting said example versions of the embodiments are referred to for e.g., as operations, steps or modules.

Similar to a server 930 described above, a client device 901 can include a processor, memory, storage device, display, input device and communication interface (e.g., e-mail interface) for connecting the client device to the Internet 928, the ISP, or LAN 922, for communication with the servers 930.

The system 900 can further include computers (e.g., personal computers, computing nodes) 905 operating in the same manner as client devices 901, wherein a user can utilize one or more computers 905 to manage data in the server 930.

Figure 10:
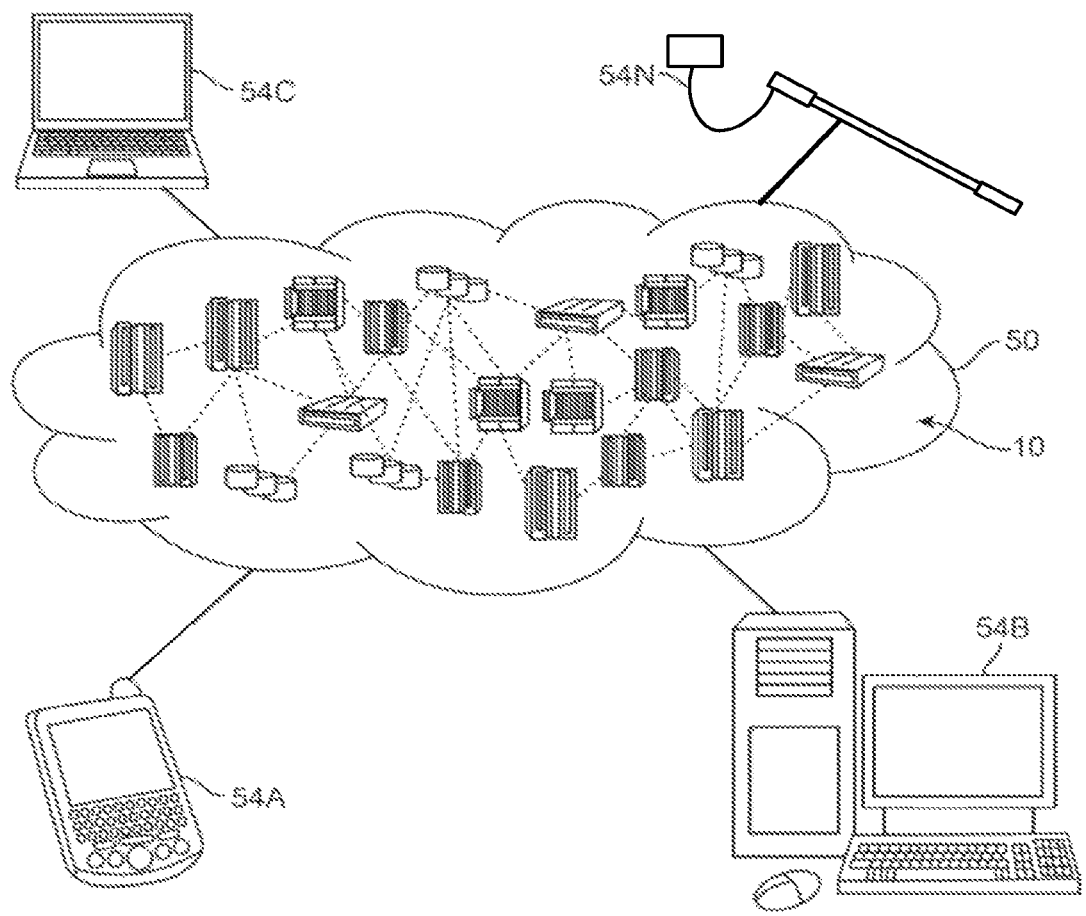
FIG. 10 depicts a cloud computing environment for implementing an embodiment of the system and process disclosed herein.

Referring now to FIG. 10, illustrative cloud computing environment 50 is depicted. As shown, cloud computing environment 50 comprises one or more cloud computing nodes 10 with which local computing devices used by cloud consumers, such as, for example, personal digital assistant (PDA), smartphone, smartwatch, set-top box, video game system, tablet, mobile computing device, or cellular telephone 54A, desktop computer 54B, laptop computer 54C, and/or handheld measurement device 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 10 are intended to be illustrative only and that computing nodes 10 and cloud computing environment 50 can communicate with any type of computerized device over any type of network and/or network addressable connection (e.g., using a web browser).

It is contemplated that various combinations and/or sub-combinations of the specific features and aspects of the above embodiments may be made and still fall within the scope of the invention. Accordingly, it should be understood that various features and aspects of the disclosed embodiments may be combined with or substituted for one another in order to form varying modes of the disclosed invention. Further, it is intended that the scope of the present invention herein disclosed by way of examples should not be limited by the particular disclosed embodiments described above.

What is claimed is:

1. A system comprising:
   a handheld sensing device comprising:
     a trace-gas sensor configured to measure ambient trace-gas concentrations, wherein the trace-gas sensor comprises tunable laser spectroscopy to detect gaseous molecules with high sensitivity;
     a handle, wherein the trace-gas sensor is disposed on a first end of the handle; and
     a grip disposed on a second end of the handle, wherein the first end of the handle is distal from the second end of the handle;
   a control electronics comprising:
     a processor having addressable memory, the processor in communication with the trace-gas sensor, wherein the processor is configured to:
       receive the measured ambient trace-gas concentrations; and
       detect elevated ambient trace-gas concentrations based on the measured ambient trace-gas concentrations; and
   an attachment device physically separated from the handheld sensing device, wherein the attachment device is configured to communicate with the handheld sensing device via a wireless connection, wherein the attachment device is configured to detachably attach to a wearable device of an operator, wherein the attachment device houses the control electronics and a power supply, and wherein the power supply is configured to provide power to the handheld sensing device.

2. The system of claim 1, wherein the trace-gas sensor measures a methane gas concentration.

3. The system of claim 1, wherein the trace-gas sensor measures at least one of the following gases: methane, ethane, propane, butane, and pentane.

4. The system of claim 1, wherein the trace-gas sensor measures at least two of the following gases: methane, ethane, propane, butane, and pentane.

5. The system of claim 1, wherein the trace-gas sensor measures a combination of gases that are representative of natural gas.

6. The system of claim 1, wherein the control electronics are housed inside the grip.

7. The system of claim 1, wherein the handheld sensing device further comprises:
   a first transceiver, wherein the processor is in communication with the trace-gas sensor via the first transceiver, and wherein the first transceiver is configured to send measured ambient trace-gas concentrations.

8. The system of claim 7, wherein the attachment device further comprises:
   a second transceiver, wherein the processor is in communication with the trace-gas sensor via the first transceiver and the second transceiver, and wherein the second transceiver is configured to receive measured ambient trace-gas concentrations.

9. The system of claim 1, wherein the wired connection is a shielded coiled cable.

10. The system of claim 1, wherein the control electronics further comprise:
    a global positioning system (GPS); and
    a connected device, wherein the connected device is in communication with at least one of: the handheld sensing device, the attachment device, and the control electronics, wherein the connected device acquires the location data from the GPS and relays it to at least one of: a first transceiver and a second transceiver, wherein the connected device is configured to display a map showing the determined location of the trace-gas source, and wherein the connected device comprises at least one of: an augmented reality (AR) device and a cloud server having at least one database;
    wherein the processor is further configured to:
      receive a location data from the GPS corresponding to the received measured ambient trace-gas concentrations;

receive a meteorological data corresponding to the received measured ambient trace-gas concentrations; and determine a location of a trace-gas source based on the detected elevated trace-gas concentration relative to ambient trace-gas concentration, the received location data, and the received meteorological data.

11. The system of claim 1, wherein the trace-gas sensor is connected to a pump.

12. A method comprising:

measuring, by a trace-gas sensor of a handheld sensing device, ambient trace-gas concentrations;

receiving, by a processor having addressable memory of the handheld sensing device, the measured ambient trace-gas concentrations, wherein receiving the measured ambient trace-gas concentrations further comprises: sending, by a first transceiver of the handheld sensing device, the measured ambient trace-gas contractions, and receiving, by a second transceiver of the attachment device, the measured ambient trace-gas contractions; and detecting, by the processor of the handheld sensing device, elevated ambient trace-gas concentrations based on the measured ambient trace-gas concentrations;

wherein the trace-gas sensor is disposed on a first end of a handle of the handheld sensing device, wherein the processor is disposed on a second end of the handle of the handheld sensing device, wherein the first end of the handle is distal from the second end of the handle;

wherein an attachment device is physically separated from the handheld sensing device, wherein the attachment device is configured to communicate with the handheld sensing device via a wireless connection, wherein the attachment device is configured to detachably attach to a wearable device of an operator, wherein the attachment device houses the control electronics and a power supply, and wherein the power supply is configured to provide power to the handheld sensing device.

13. The method of claim 12 further comprising:

receiving, by the processor, a location data from a global positioning system (GPS) corresponding to the received measured ambient trace-gas concentrations; and receiving, by the processor, a meteorological data corresponding to the received measured ambient trace-gas concentrations.

14. The method of claim 13 further comprising:

determining, by the processor, a location of a trace-gas source based on the detected elevated ambient trace-gas concentration, the received location data, and the received meteorological data.

15. The method of claim 14 further comprising:

displaying, by a connected device in communication with the processor, a map showing the determined location of the trace-gas source.

16. A system comprising:

a handheld sensing device comprising:

a trace-gas sensor configured to measure ambient trace-gas concentrations;

a handle, wherein the trace-gas sensor is disposed on a first end of the handle;

a grip disposed on a second end of the handle, wherein the first end of the handle is distal from the second end of the handle; and an attachment device physically separated from the handheld sensing device, wherein the attachment device is configured to communicate with the handheld sensing device via a wireless connection, wherein the attachment device is configured to detachably attach to a wearable device of an operator, wherein the attachment device is in communication with the handheld sensing device via the wireless connection, and wherein the attachment device comprises:

a processor having addressable memory, the processor in communication with the trace-gas sensor, wherein the processor is configured to:

receive the measured ambient trace-gas concentrations;

receive a location data corresponding to the received measured ambient trace-gas concentrations;

receive a meteorological data corresponding to the received measured ambient trace-gas concentrations;

detect elevated ambient trace-gas concentrations based on the measured ambient trace-gas concentrations;

determine a location of a trace-gas source based on the detected elevated ambient trace-gas concentration, the received location data, and the received meteorological data;

wherein the processor is in communication with the trace-gas sensor via the first transceiver and the second transceiver, wherein the first transceiver is configured to send measured ambient trace-gas concentrations, and wherein the second transceiver is configured to receive measured ambient trace-gas concentrations;

a connected device, wherein the connected device is in communication with at least one of: the handheld sensing device and the attachment device, wherein the connected device comprises at least one of: a smartphone, a tablet, an augmented reality (AR) device, and a virtual reality (VR) device, and wherein the connected device is configured to display a map showing the determined location of the trace-gas source.

* * * * *